(12) United States Patent
Meyer et al.

(10) Patent No.: US 7,499,751 B2
(45) Date of Patent: Mar. 3, 2009

(54) CARDIAC SIGNAL TEMPLATE GENERATION USING WAVEFORM CLUSTERING

(75) Inventors: Scott A. Meyer, Rochester, MN (US); Yanting Dong, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 219 days.

(21) Appl. No.: 11/116,544

(22) Filed: Apr. 28, 2005

(65) Prior Publication Data

US 2006/0247707 A1    Nov. 2, 2006

(51) Int. Cl.
*A61N 1/08*    (2006.01)

(52) U.S. Cl. .............................. 607/28; 607/11; 607/27; 600/510

(58) Field of Classification Search ................... 607/11, 607/27, 28; 600/510
See application file for complete search history.

(56) References Cited

U.S. PATENT DOCUMENTS

| | | | |
|---|---|---|---|
| 4,878,497 A | 11/1989 | Callaghan et al. |
| 5,184,615 A | 2/1993 | Nappholz et al. |
| 5,217,021 A | 6/1993 | Steinhaus et al. |
| 5,222,493 A | 6/1993 | Sholder |
| 5,324,310 A | 6/1994 | Greeninger et al. |
| 5,350,410 A | 9/1994 | Kleks et al. |
| 5,431,693 A | 7/1995 | Schroeppel |
| 5,443,485 A | 8/1995 | Housworth et al. |
| 5,683,431 A | 11/1997 | Wang |
| 5,779,645 A | 7/1998 | Olson et al. |
| 5,817,027 A | 10/1998 | Arand et al. |
| 5,857,977 A | 1/1999 | Caswell et al. |
| 6,038,474 A | 3/2000 | Zhu et al. |
| 6,076,014 A | 6/2000 | Alt |
| 6,101,416 A | 8/2000 | Sloman |
| 6,128,535 A | 10/2000 | Maarse |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,192,275 B1 | 2/2001 | Zhu et al. |
| 6,221,011 B1 | 4/2001 | Bardy |

(Continued)

FOREIGN PATENT DOCUMENTS

EP    0468720    1/1992

(Continued)

OTHER PUBLICATIONS

Mitchell I. Cohen et al. *Capture Management Efficacy in children and young adults with endocardial and unipolar epicardial systems.* Europace, vol. 6, pp. 248-255 (2004).

(Continued)

*Primary Examiner*—Carl H Layno
*Assistant Examiner*—Yun Haeng Lee
(74) *Attorney, Agent, or Firm*—Hollingsworth & Funk, LLC

(57) ABSTRACT

Cardiac devices and methods using cardiac waveform clustering for template generation are described. A method of characterizing a cardiac response involves delivering pacing pulses to heart, the pulses having an energy greater than a capture threshold. Cardiac signals are sensed following the pulses. Cardiac signal characteristics, waveforms, and/or features are clustered into a plurality of clusters. A cardiac response template is formed using one or more of the plurality of clusters.

21 Claims, 15 Drawing Sheets

U.S. PATENT DOCUMENTS

| | | |
|---|---|---|
| 6,226,551 B1 | 5/2001 | Zhu et al. |
| 6,238,419 B1 | 5/2001 | Lindgren |
| 6,270,457 B1 | 8/2001 | Bardy |
| 6,275,731 B1 | 8/2001 | Zhu et al. |
| 6,277,072 B1 | 8/2001 | Bardy |
| 6,280,380 B1 | 8/2001 | Bardy |
| 6,312,378 B1 | 11/2001 | Bardy |
| 6,312,388 B1 | 11/2001 | Marcovecchio et al. |
| 6,324,427 B1 | 11/2001 | Florio |
| 6,336,903 B1 | 1/2002 | Bardy |
| 6,345,201 B1 | 2/2002 | Sloman et al. |
| 6,358,203 B2 | 3/2002 | Bardy |
| 6,368,284 B1 | 4/2002 | Bardy |
| 6,398,728 B1 | 6/2002 | Bardy |
| 6,434,428 B1 | 8/2002 | Sloman et al. |
| 6,440,066 B1 | 8/2002 | Bardy |
| 6,449,503 B1 | 9/2002 | Hsu |
| 6,456,881 B1 | 9/2002 | Bornzin et al. |
| 6,466,820 B1 | 10/2002 | Juran et al. |
| 6,480,734 B1 | 11/2002 | Zhang et al. |
| 6,505,071 B1 | 1/2003 | Zhu et al. |
| 6,512,953 B2 | 1/2003 | Florio et al. |
| 6,567,701 B2 | 5/2003 | Vonk |
| 6,615,082 B1 | 9/2003 | Mandell |
| 6,618,619 B1 | 9/2003 | Florio et al. |
| 6,738,669 B1 | 5/2004 | Sloman et al. |
| 6,973,350 B1 | 12/2005 | Levine et al. |
| 6,975,904 B1 * | 12/2005 | Sloman ................. 607/28 |
| 7,027,868 B2 | 4/2006 | Rueter et al. |
| 7,191,004 B2 | 3/2007 | Kim et al. |
| 7,319,900 B2 | 1/2008 | Kim et al. |
| 2001/0049542 A1 | 12/2001 | Florio et al. |
| 2002/0095188 A1 | 7/2002 | Mower |
| 2002/0138111 A1 | 9/2002 | Greenhut et al. |
| 2002/0183798 A1 | 12/2002 | Vonk |
| 2003/0050671 A1 | 3/2003 | Bradley |
| 2003/0083710 A1 | 5/2003 | Ternes et al. |
| 2003/0083711 A1 | 5/2003 | Yonce et al. |
| 2003/0125777 A1 | 7/2003 | Ding et al. |
| 2004/0082975 A1 | 4/2004 | Meyer et al. |
| 2004/0127805 A1 | 7/2004 | MacAdam et al. |
| 2004/0127950 A1 | 7/2004 | Kim et al. |
| 2004/0171959 A1 | 9/2004 | Staler et al. |
| 2004/0172065 A1 | 9/2004 | Sih et al. |
| 2004/0243014 A1 * | 12/2004 | Lee et al. .................. 600/510 |
| 2004/0254611 A1 * | 12/2004 | Palreddy et al. ............... 607/4 |
| 2004/0260351 A1 | 12/2004 | Holmstrom et al. |
| 2005/0004612 A1 * | 1/2005 | Scholten et al. ............... 607/28 |
| 2005/0131476 A1 * | 6/2005 | Kim et al. .................... 607/27 |
| 2005/0131477 A1 * | 6/2005 | Meyer et al. ................. 607/27 |
| 2005/0131478 A1 * | 6/2005 | Kim et al. .................... 607/27 |
| 2005/0256413 A1 * | 11/2005 | Astrom et al. ............. 600/509 |
| 2006/0129194 A1 * | 6/2006 | Zhang ........................ 607/17 |
| 2006/0129195 A1 * | 6/2006 | Sathaye et al. ............... 607/17 |
| 2006/0129196 A1 * | 6/2006 | Dong et al. .................. 607/28 |
| 2006/0247695 A1 | 11/2006 | Stalsberg et al. |
| 2007/0016261 A1 | 1/2007 | Dong et al. |

FOREIGN PATENT DOCUMENTS

| | | |
|---|---|---|
| EP | 1 291 038 A | 3/2003 |
| WO | WO 2004/026398 | 4/2004 |
| WO | WO 2005/058412 | 6/2005 |
| WO | WO 2006/065707 | 6/2006 |

OTHER PUBLICATIONS

Splett et al. "Determination of Pacing Capture in Implantable Defibrillators: Benefit of Evoked Response Detection Using RV Coil to Can Vector," *Pace*, vol. 23, pp. 1645-1650. Nov. 2000.

* cited by examiner

CARDIAC SIGNAL TEMPLATE GENERATION USING WAVEFORM CLUSTERING

FIELD OF THE INVENTION

The present invention relates generally to implantable medical devices and, more particularly, to cardiac devices and methods using cardiac waveform clustering for template generation.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Detecting if a pacing pulse "captures" the heart and produces a contraction allows the cardiac rhythm management system to adjust the energy level of pace pulses to correspond to the optimum energy expenditure that reliably produces capture. Further, capture detection allows the cardiac rhythm management system to initiate a back-up pulse at a higher energy level whenever a pace pulse does not produce a contraction.

A fusion beat is a cardiac contraction that occurs when two cardiac depolarizations of a particular chamber, but from separate initiation sites, merge. At times, a depolarization initiated by a pacing pulse may merge with an intrinsic beat, producing a fusion beat. Fusion beats, as seen on electrocardiographic recordings, exhibit various morphologies. The merging depolarizations of a fusion beat do not contribute evenly to the total depolarization.

Pseudofusion occurs when a pacing stimulus is delivered on a spontaneous P wave during atrial pacing or on a spontaneous QRS complex during ventricular pacing. In pseudofusion, the pacing stimulus may be ineffective because the tissue around the electrode has already spontaneously depolarized and is in its refractory period.

Capture detection, for example, involves discriminating captured beats from fusion/pseudofusion beats, intrinsic beats, noise, and noncapture. Discriminating between various cardiac responses can be accomplished by comparing cardiac signals to templates representative of various response types. The present invention involves methods and systems for creating templates used in connection with recognizing various cardiac responses.

SUMMARY OF THE INVENTION

The present invention involves various cardiac devices and methods using cardiac waveform clustering for template generation. A method of characterizing a cardiac response in accordance with the present invention involves delivering pacing pulses to heart, the pacing pulses having an energy greater than a capture threshold. Cardiac signals are sensed following the pacing pulses. One or more initial templates may be selectively updated using the sensed cardiac signals. A cardiac response template may be formed using one or more selected templates. Selectively updating the initial templates may involve using selected ones of the sensed cardiac signals to update a particular template. Embodiments may further involve selectively updating the templates by comparing the sensed cardiac signals to each of the templates, and selectively updating the templates using the cardiac signals based on the comparison, such as by comparing cardiac signal features to template features and/or by determining a similarity between each template and each cardiac signal and selectively updating a particular template having a particular similarity to a particular cardiac signal.

Selectively updating the templates may involve associating a counter with each template and incrementing the counter associated with a particular template if the particular template is updated. Characterizing the cardiac response using the selected template may involve characterizing the cardiac response using a particular template correlated to a higher number of cardiac signals than other templates. The selected template may be used to classify a cardiac response to pacing beat by beat, during capture threshold testing, and/or for automatic capture verification.

Other methods of characterizing a cardiac response to pacing in accordance with the present invention involve delivering pacing pulses to a heart sufficient in energy to effect capture and sensing cardiac signals respectively following delivery of the pacing pulses. The cardiac signals are clustered, defining a plurality of clusters, so that cardiac response templates may be formed using a selected one or more of the plurality of clusters. One or more features of the cardiac signals may be used to define the plurality of clusters, such as peak times of the cardiac signals, peak times associated with negative polarity peaks and/or positive polarity peaks, peak-amplitudes of the cardiac signals, or other features or signal attributes. A cardiac response template may be formed using selected clusters by forming the cardiac response template using a cluster associated with a greatest number of cardiac signals having similar characteristics.

Further embodiments of the present invention are directed to devices for characterizing a cardiac response to pacing. The device may include a sensing system configured to sense cardiac signals following pacing pulses delivered to a heart, having a processor coupled to the sensing system. The processor may be configured to selectively update a plurality of templates using the cardiac signals, and to characterize the cardiac response to pacing using a selected template of the templates. The processor may further be configured to provide one or more initial templates and selectively update the initial templates. The processor may be configured to compare the cardiac signals from a paced response to each of the templates and to selectively update the templates using the cardiac signals based on the comparison.

Other embodiments provide for the processor to be configured to determine a similarity between each template and each cardiac signal, and to update a particular template having a particular similarity to a particular cardiac signal. The processor may be configured to characterize the cardiac response using a template selected by a criterion, such as by matching a predetermined number cardiac signals before other templates are matched to the predetermined number of cardiac signals.

Yet another embodiment involves system for characterizing a cardiac response to pacing. The system includes a pulse generator configured to deliver pacing pulses to a heart sufficient in energy to effect capture. A sensor system is configured to sense cardiac signals respectively following delivery of the pacing pulses. A processor is coupled to the sensor system and is configured to cluster the cardiac signals to define a plurality of clusters and to form a cardiac response template using a selected one or more of the plurality of clusters.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
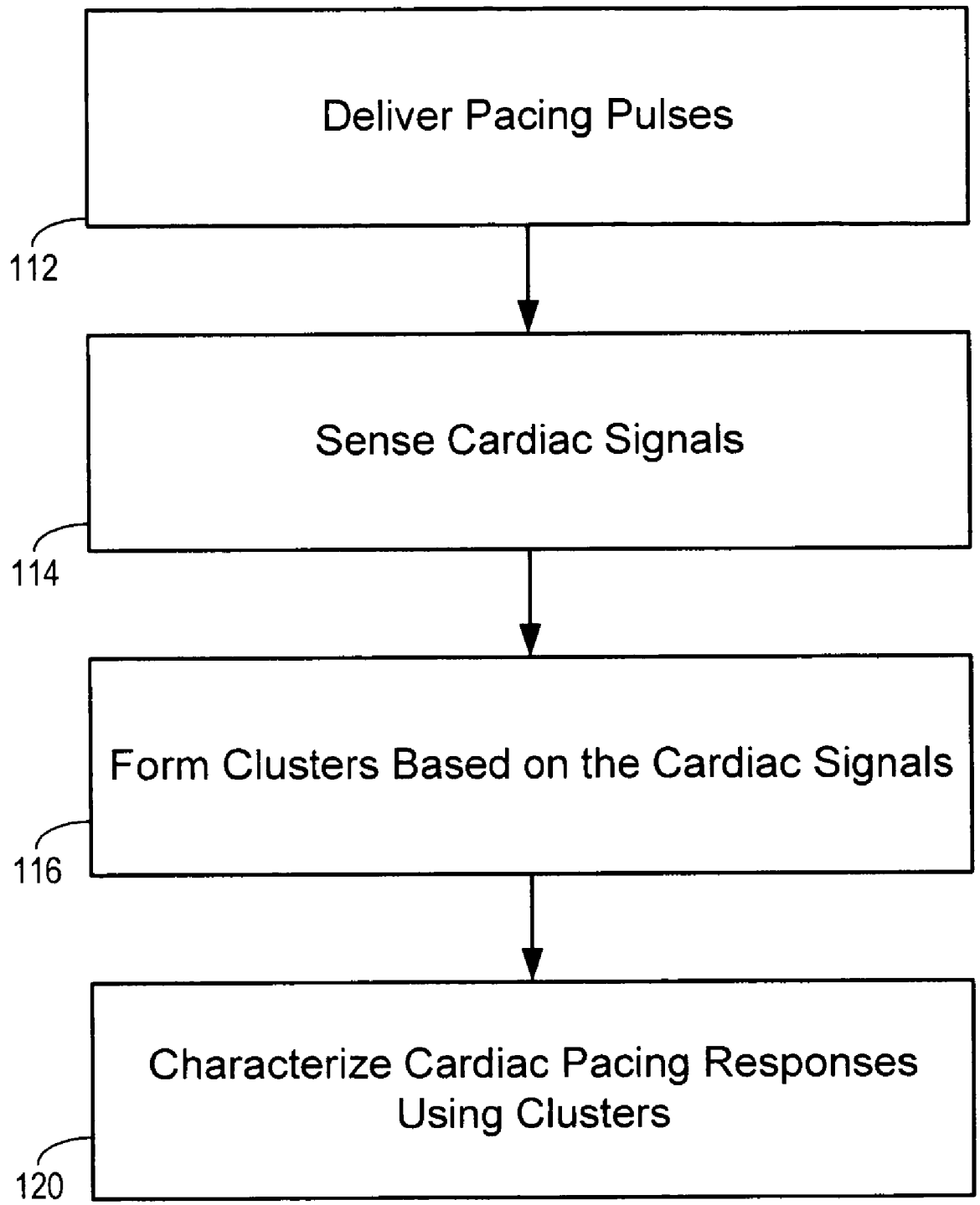
FIGS. 1A and 1B are flowcharts illustrating methods using cardiac waveform clustering for template generation in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMETS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Recognition of various cardiac conditions may rely on the consistent morphology of the type of cardiac signal associated with that condition. For example, morphology templates may be formed based on samples and/or characteristic features of a cardiac signal associated with a particular cardiac condition. A cardiac device may later compare a sensed cardiac signal to a morphology template and determine that the cardiac condition associated with the morphology template exists if the sensed cardiac signal is sufficiently similar to the morphology template. Similarly, if the sensed cardiac signal is sufficiently different from the morphology template, a condition exclusive of the cardiac condition associated with the morphology template can be determined.

Determination of the cardiac response to a pacing pulse applied to a heart chamber may be based on morphological features of the cardiac signal sensed in the heart chamber after pacing. The cardiac response to a pacing pulse may include noncapture without intrinsic activity, capture, fusion, pseudofusion, and noncapture with intrinsic activity, for example. Morphology templates can be used to represent one or more of these types of cardiac pacing responses. Cardiac signals sensed after pacing may be compared to one or more morphology templates. In one implementation, samples and/or characteristic features of a cardiac signal are extracted from the cardiac signal and are compared to samples and/or features associated with one or more of morphology templates characterizing a particular type of cardiac pacing response. The type of cardiac pacing response may be determined based on the similarity of the samples and/or characteristic features of the sensed cardiac signal to one of the morphology templates.

Cardiac response classification may be implemented by a pacemaker, defibrillator, or other cardiac rhythm management (CRM) device to determine the cardiac response to an applied electrical pacing stimulus. Embodiments of the invention are directed to cardiac devices and methods using clustering of the cardiac signals or signal features to generate templates characterizing various types of cardiac responses to pacing.

Several functions of CRM devices may rely on the consistency of cardiac beats to detect certain conditions. For example, cardiac pacing response characterization algorithms may rely on templates of the heart's response as the basis for determining whether a pacing pulse produces a captured response or other response. However, the morphology of the captured response signal may vary across patients, and change over time. Therefore, templates characterizing the captured response (or other types of cardiac signals) may need to be regularly generated or updated for every patient.

A flowchart illustrating a method of forming templates in accordance with embodiments of the invention is illustrated in FIG. 1A. A plurality of pacing pulses is delivered 112 to the heart. The cardiac signals associated with the pacing pulses are sensed 114. Clusters of similar cardiac signals are formed 116. The clusters may be used to generate 120 templates characterizing one or more types of cardiac pacing responses. Clustering the cardiac signals may be performed using a variety of techniques, including analog and/or digital processing techniques. Several exemplary embodiments directed to clustering processes are described herein, however, other processes may additionally or alternatively used and are considered to be within the scope of the present invention.

Figure 1B:
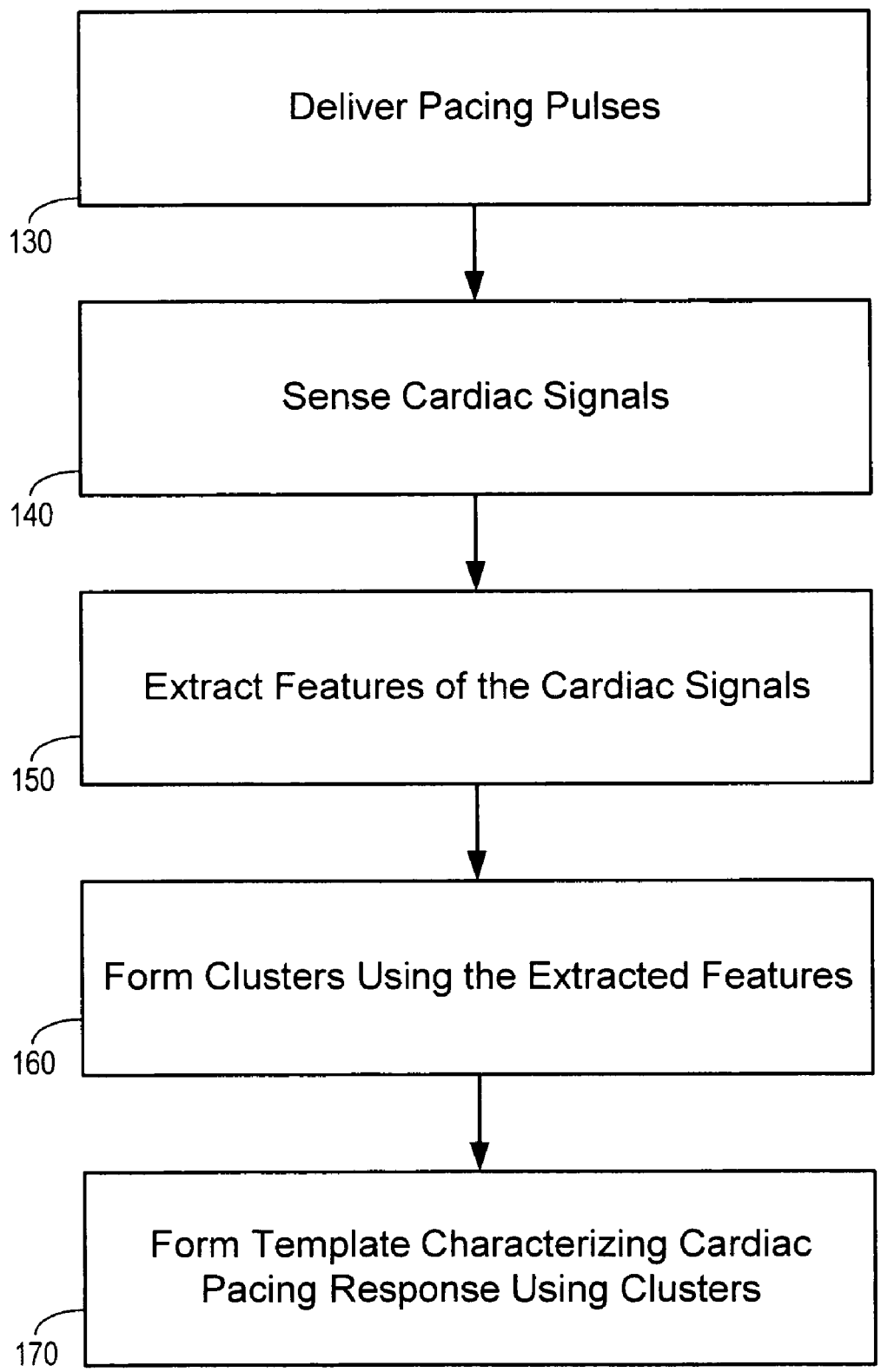

FIG. 1B illustrates another method of forming a template in accordance with embodiments of the invention. A plurality of pacing pulses are delivered 130 to the heart and cardiac signals are sensed 140 following each pacing pulse. Features of the cardiac signals are extracted 150. The cardiac signal features are used to form 160 a plurality of clusters. A cardiac pacing response is characterized 170 using one or more of the plurality of clusters.

Consider generating a template for a captured response as an example. One goal is to generate the template for a captured response, and at the same time, avoid the influence of fusion/pseudofusion beats, noise or other types of responses. Including fusion beats in the response template generation adds an error component to the template. Templates that include information from responses other than the desired response may result in less than optimal template correlation to future captured beats, and contribute to impaired discrimination capability.

Template generating in accordance with the present invention reduces the inclusion of undesired response signals. Reducing undesired signals from inclusion to a particular template may be accomplished by recognizing that captured responses have consistent morphology. Clustering signal features according to similarities provides a signal exclusion criterion for template generation. Clustering may be performed using techniques such as a K-Means clustering algorithm, self-organizing map algorithms, or other data clustering algorithms.

Continuing with the example of generating a captured response template, suppose that a sequence of N suprathreshold paces are delivered, N being a positive integer. A clustering algorithm, which may be applied after all N paces are delivered, or applied during response signal collection, may be applied to the extracted features of the pace response signals in accordance with the present invention. After N paces are delivered, a template may be generated using only the response signals with features within a cluster, and exclude all other signals from the template generation. Applied during response signal collection, a template may be generated using only the response signals with features within a cluster, thereby building confidence in the cluster, adjusting the template with each select response signal, and excluding all other signals from the template generation. Multiple templates may be created concurrently by creating a template for each cluster, or selected clusters.

For example, responses to all N paces may be recorded, and processed through a clustering algorithm that separates the signals into three clusters, captured response, fusion response, and other response. If all the pace pulses are known a-priori to be above the capture threshold and the pacing parameters are chosen to promote capture, then it would be expected that the number of captured responses would be predominant, followed by the number of fusion/pseudofusion beats, and possibly include some other responses such as noise or unknown responses. A capture template may be generated using the signals in the predominant cluster. For example, the cluster with the largest number of similar pace responses may be selected as the cluster used to generate the captured response template.

Other criteria may also be imposed, such as a cluster is only used if a predetermined number of signals are associated with the cluster, such as a number P, where P is a positive integer less than N, using the above example. Cardiac waveform clustering for template generation in accordance with the present invention provides an accurate template of heart response, and reduces the influence of undesirable beats on the estimate of the template.

Figure 2A:
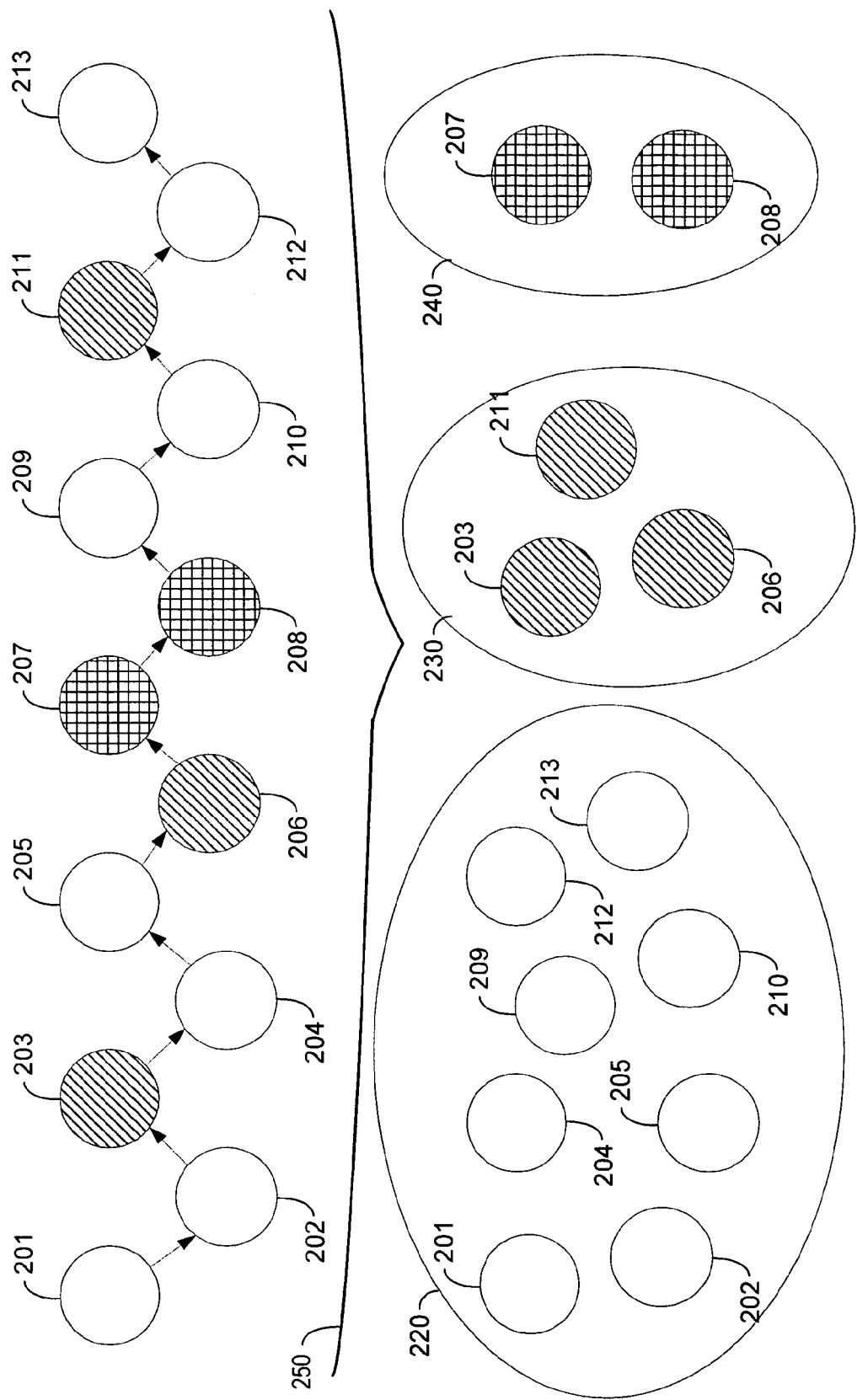
FIG. 2A is a concept diagram illustrating the use of clustering for template creation in accordance with embodiments of the invention.

The use of clustering for template creation is illustrated by the concept diagram of FIG. 2A. In FIG. 2A, the measured cardiac signals responsive to thirteen successive paces are illustrated as circles 201-213. Each circle 201-213 may correspond to a feature of the cardiac signals responsive to the thirteen paces, a sequence of features points, or the entire cardiac waveform. The circle 201 may correspond to a feature, feature points or waveform of a first paced response, the second circle 202 may correspond to a feature, feature points or waveform of a second paced response. In some embodiments, the pacing and response measurement process continues until the circle 213 is measured, corresponding to a feature, feature points or waveform of the thirteenth paced response. In other embodiments, clustering may be performed after each measurement in a beat by beat manner.

Responses 201, 202, 204, 205, 209, 210, 212, and 213 are grouped into a cluster 220 based on the similarity of responses 201, 202, 204, 205, 209, 210, 212, and 213. Responses 203, 206, and 211 are grouped into a cluster 230. Responses 207 and 208 are grouped into a cluster 240. The responses 201, 202, 204, 205, 209, 210, 212, and 213 of cluster 220 may be determined to include captured responses, the responses 203, 206, and 211 of cluster 230 may be determined to represent fusion/pseudofusion beats, and the responses 207 and 208 of cluster 240 may be noisy signals or unknown cardiac responses.

The similarity of responses in a cluster may be determined based on one or more morphological features of the cardiac signal. In one implementation, the system may determine the similarity of one or more of a peak width, peak amplitude and peak timing. In another implementation, a sequence of samples from one cardiac signal may be compared to a corresponding sequence of samples from another cardiac signal to determine if the signals are similar.

Clustering the cardiac waveform features, sequence of feature points or cardiac waveforms involves grouping the features, sequence of feature points or cardiac waveforms that are similar.

According to one implementation, the process of using clustering to form a template may involve determining corresponding cardiac signal features of a number of cardiac signals associated with a particular type of cardiac pacing response and clustering the cardiac signal features to form a template. The clustering may be performed by determining the relationships between the cardiac signal feature points and forming clusters of the feature points based on the relationships. Clustering in this manner may be performed using a variety of clustering algorithms, including K-means algorithms, self-organizing map algorithms, or other data clustering algorithms.

According to another implementation, clustering may be performed by forming an initial template, for example, using one or more feature points of a first detected cardiac signal and clustering additional feature points of additional cardiac signals with the initial feature point based on a set of rules. For example, an additional feature point may be clustered with a feature point of the initial template if it is sufficiently similar to the corresponding feature point of the initial template. Similarity in this implementation may be determined by an externally determined set of rules that are not necessarily based on the relationships between feature points.

Figure 2B:
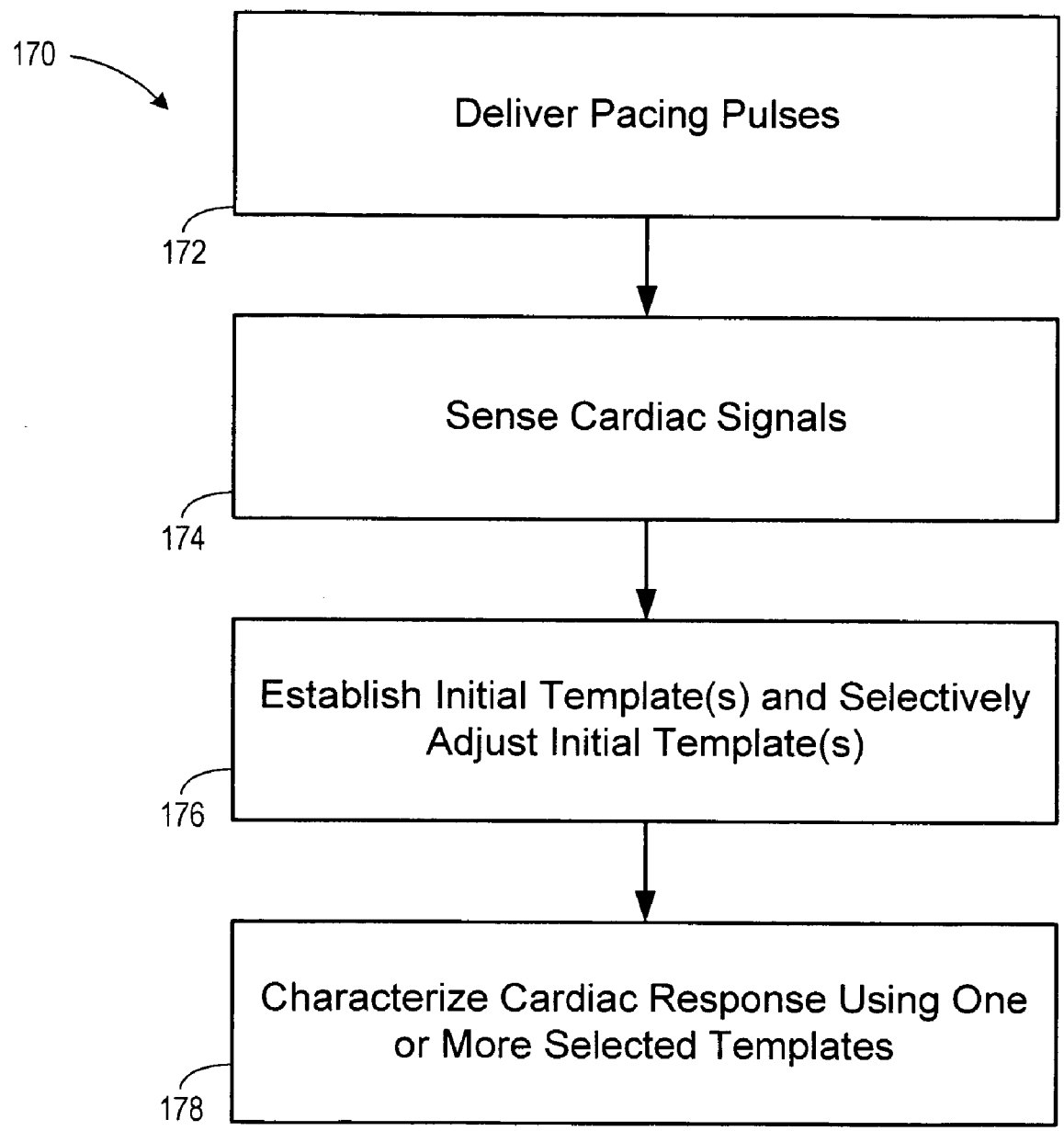
FIG. 2B is a flowchart of a method of using cardiac waveform clustering for template generation in accordance with embodiments of the invention.

FIG. 2B is a flowchart of a method 170 of using cardiac waveform clustering for template generation in accordance with embodiments of the invention. Two or more pacing pulses 172 are delivered to a patient's heart, at a level that exceeds the capture threshold. Cardiac response signals 174 are sensed, and measurements are made of cardiac signal features. One or more initial templates are provided. The one or more initial templates may be generated using one or more cardiac signals, may be estimated, retrieved from memory, formed according to a rules-based process, or formed by other methods. One or more of the initial templates 176 are incrementally adjusted using select cardiac response signals. Each sensed cardiac signal may be used to adjust 176 a particular template of the one or more templates. Adjustment of the templates may be implemented using a clustering algorithm and may be based on the measurements of the cardiac signal features. One or more of the templates 178 may be selected for characterizing cardiac responses. In one example, one of the templates may be selected to characterize a captured response. In another example, a first template formed via the clustering process may be used to characterize a captured response and a second template may be used to characterize a fusion/pseudofusion response.

Figure 2C:
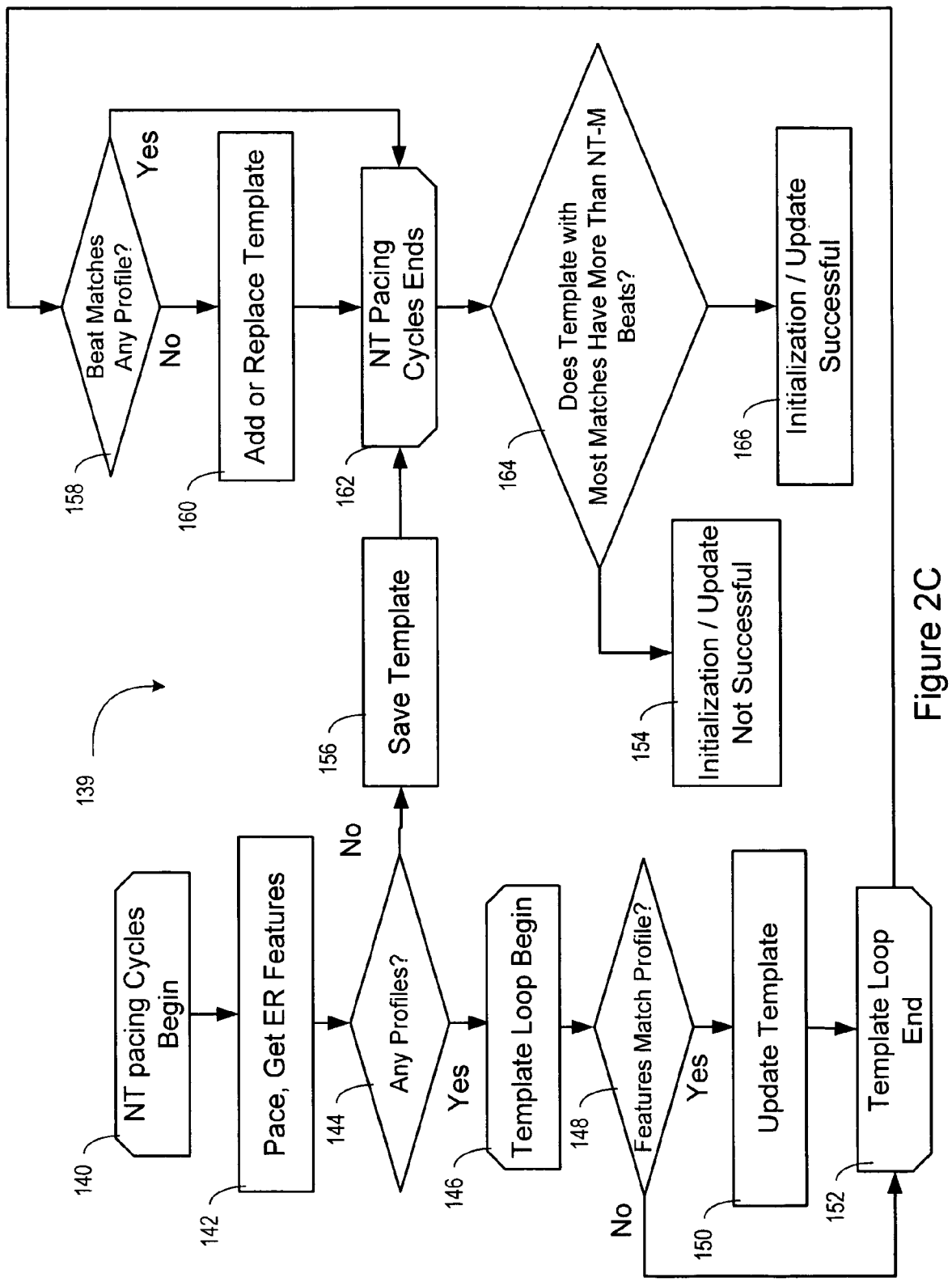
FIGS. 2C and 2D are flowcharts illustrating methods of generating templates in accordance with embodiments of the invention.

FIG. 2C is a flowchart of a method 139 of generating templates in accordance with embodiments of the present invention. An integer number NT of pacing cycles are selected to begin 140 the template generation process using a NT pacing cycle loop 140-162. A pace 142 is delivered to the heart, and the cardiac signal associated with the pacing pulse is sensed. Features or samples of the cardiac signal associated with the pacing pulse are acquired. If no template has been created or otherwise provided, then the cardiac signal is used to generate a template. The initial template 156 is saved, and the pacing cycle continues after incrementing the NT count at pacing cycle loop end 162. Information related to the cardiac signal may also be stored and associated with the template, such as the pacing energy (voltage and/or pulse width) of the pacing pulse, pace rate, AV delay, VV interval and/or any other pacing parameter settings or measurements. If a template has already been formed or provided, then the process continues to the loop represented by blocks 146-152. In loop 146-152, the cardiac signal is compared to any existing templates at a check 148. If the check 148 finds that the cardiac signal matches an existing template, the template is adjusted 150 to improve the estimate of the template, and the loop 146-152 continues. Adjusting the template may be accomplished, for example, by averaging feature values or performing a weighted average of feature values. Characteristics represented by the stored information that is related to the cardiac signal and associated with the template, such as pacing parameter settings or measurements, may also be adjusted.

If no template matches at check 148 after all existing templates have been compared to the cardiac signal, a decision 158 is made to add or replace a template 160. A new template may be created, either by adding or estimating a new template, or replacing an old template. In various implementations, the replaced template may comprise the oldest template or the template with the least number of matched beats. If all templates have at least a minimum number of matched beats, e.g., about one beat, then the cardiac cycle may be ignored with no template replaced. The maximum number of templates used by method 139 may be limited to a predetermined number.

In one implementation, the NT pacing cycle loop 140-162 continues until all NT paces are completed or when some other criteria are satisfied. For example, the NT pacing cycle loop may terminate successfully (with a template recommendation) if a template has been matched to more than NT-M beats, where M represents the number of allowed mismatched beats. In another embodiment, the pacing cycle loop 140-162 may terminate unsuccessfully (without a template recommendation) if the maximum number of template matches is below a predetermined number after a certain number of pacing cycles. More specifically, the pacing cycle loop 140-162 may terminate unsuccessfully if the maximum number of template matches is below about one after about three pacing cycles.

After all NT paces are completed in the NT pacing cycle loop 140-162, a decision 164 is made to determine if one or more of the templates meets criteria for saving as templates representative of particular types of cardiac pacing responses. For example, if a template is desired to characterize a captured response, a criterion may comprise: out of NT paced beats of the NT pacing cycle loop 140-152, if a template has been updated (NT-M) times, where M represents the designated number of mismatched beats that form a failed attempt at template generation, then the template is accepted as an captured response template, and the captured response template generation is successful 166. Using this criterion, if a template has not been updated (NT-M) times, then the template is not accepted as a captured response template, and the template generation is not successful 154. Additional criteria may be applied to terminate template generation early. If at check 148, a designated M mismatches are realized before NT pacing cycles complete, or the first cycle after the initial saved template, 156, does not match, then a failed attempt at template generation results.

Each pacing cycle loop 140-162 represents an attempt to generate a template. After a predetermined number of pacing cycle loops 140-162 are performed, attempts to generate the template may be suspended for a period of time or abandoned.

Figure 2D:
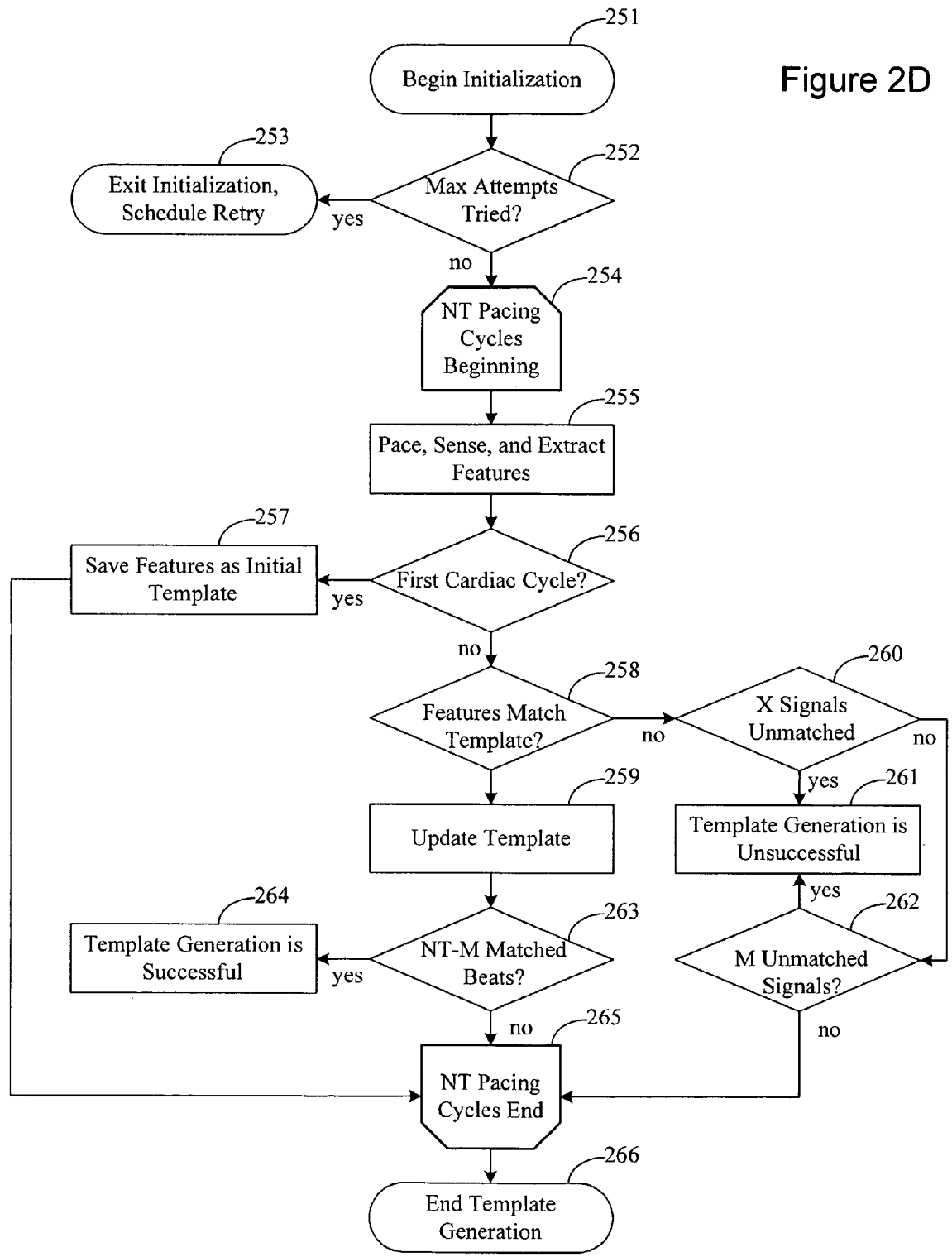

FIG. 2D is a flowchart illustrating a method for generating a template during threshold testing according to embodiments of the invention. After beginning 251 the template generation process, a check is performed 252 to see if a maximum number of attempts to generate the template have been tried. If so, the process exits 253 and a threshold test may be rescheduled for a later time.

If the maximum number of attempts have not been attempted 252, then a loop 254-265 of NT pacing cycles is initiated 254. A pacing pulse 255 is delivered and the cardiac signal following the pacing pulse is sensed. Features are extracted from the sensed cardiac signal. If it is the first cycle 256 in the loop 254-265 of NT pacing cycles, then the extracted features are saved 257 as an initial template. If it is not the first cycle 256 in the loop 254-265 of NT pacing cycles, then a check is performed 258 to determine if the features of the sensed cardiac signal for the cycle are similar to the stored template features. If the features of the sensed cardiac signal are 258 sufficiently similar to the stored template features, then the template features are updated 259 using the features of the sensed cardiac signal.

If the cardiac signal features of NT-M cycles are similar to 263 the template features, then the template generation is successful 264.

If the cardiac signal features of the cardiac cycle are not similar 258 to the template features, then a check is performed 260 based on the number of cardiac cycles following formation of the initial template. If the cardiac signal features of a predetermined number of cycles following formation of the initial template are not 260 similar to the template, or if there have been M cardiac signal that are not 262 similar to the template then the template generation attempt is terminated 261 unsuccessfully.

Figure 3:
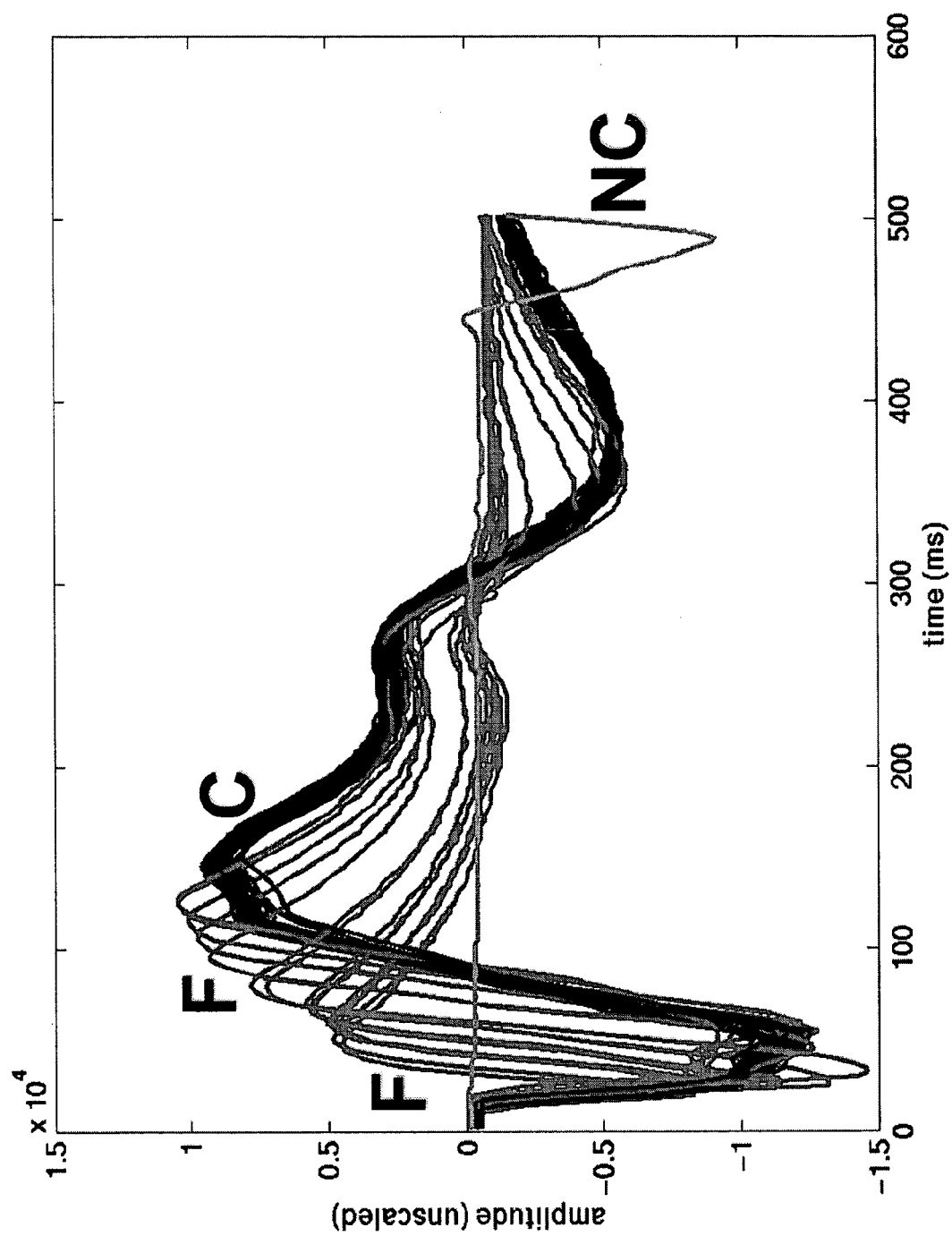
FIG. 3 is a graph illustrating a number of cardiac signals representing captured responses, fusion responses, and an intrinsic response that may be utilized for cardiac response template generation in accordance with embodiments of the invention.
Figure 4:
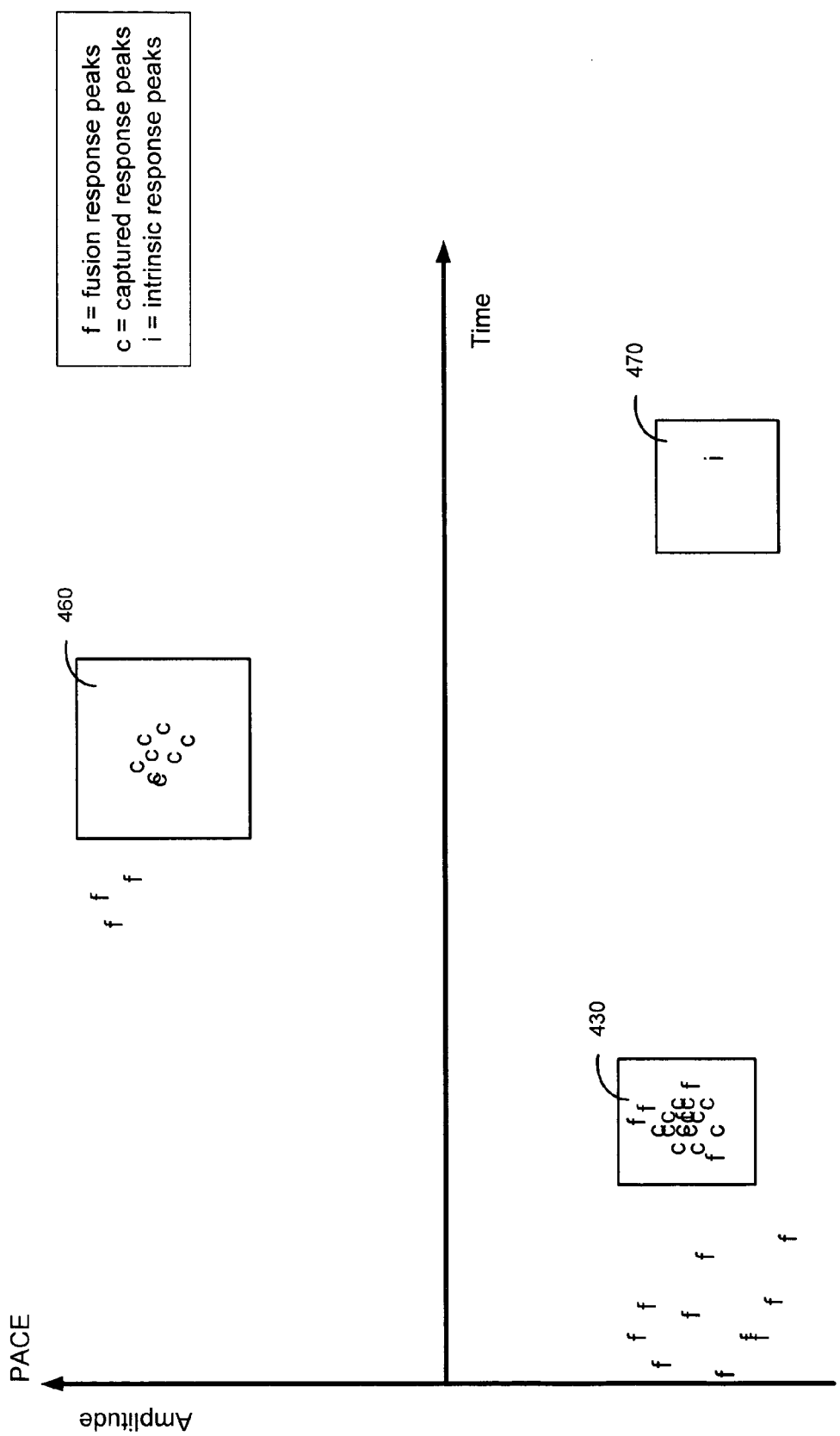
FIG. 4 is a graph that depicts the peaks of the captured signals, the fusion beats, and the intrinsic response illustrated in FIG. 3.
Figure 5:
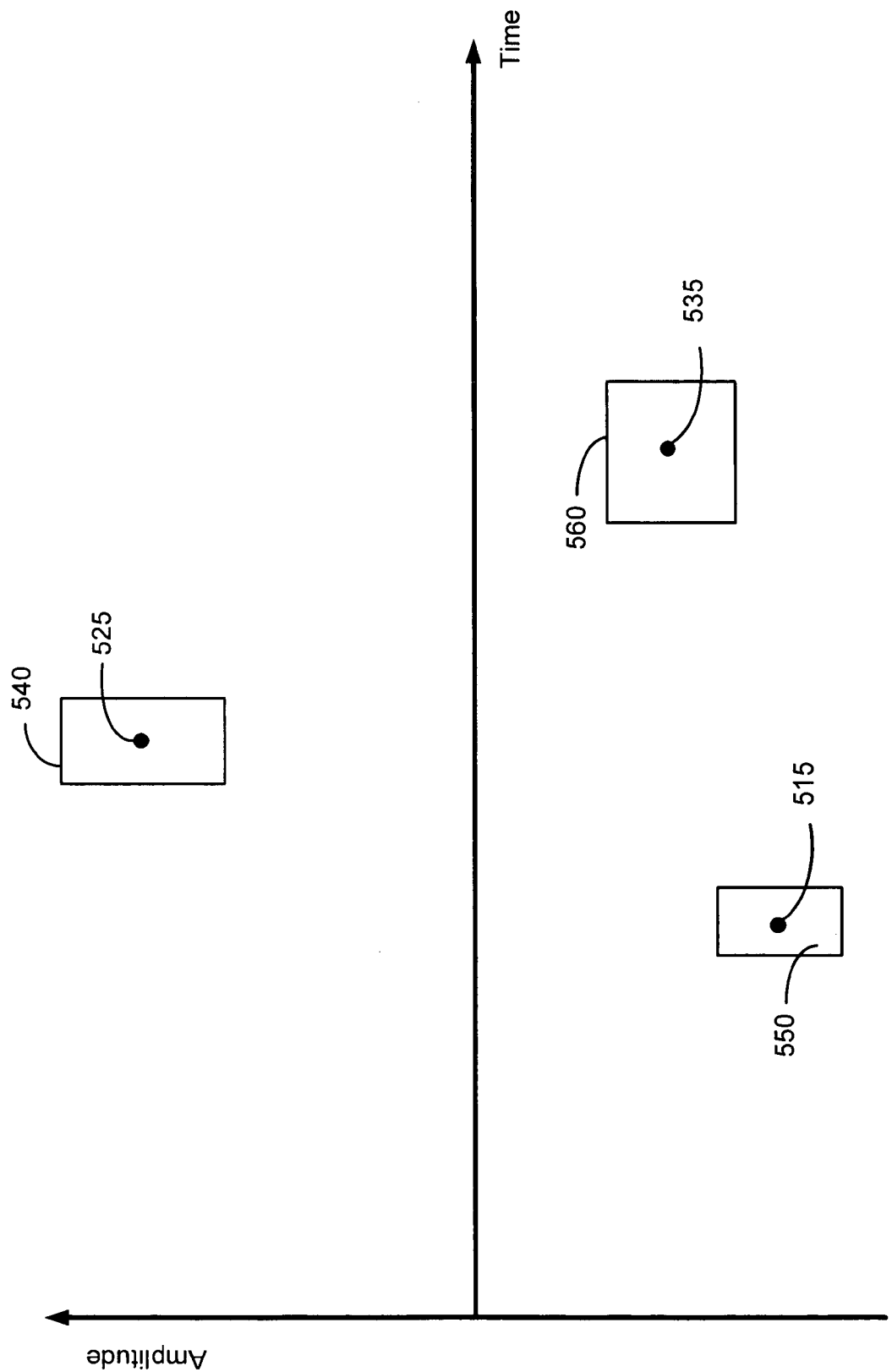
FIG. 5 illustrates cardiac response detection windows that may be used to form templates in accordance with embodiments of the invention.

The graphs of FIGS. 3 through 5 illustrate the process of forming templates according to the methods of the present invention. FIG. 3 is a graph illustrating a number of cardiac signals representing captured responses, identified by the letter C, fusion responses, identified by the letter F, and a non-captured, intrinsic response, identified by the letters NC. Features of these responses may be clustered to form templates representative of each the different types of responses, or templates representative of some of the responses and exclusive of others; in either case, allowing discrimination of the various responses. In this example, the particular features that are clustered include peak amplitudes and peak timings of the cardiac signals. The clustered peaks are used to form templates comprising one or more classification windows defined in terms of amplitude and time.

FIG. 4 is a graph that depicts the peaks of the captured, fusion, and non-captured intrinsic responses illustrated in FIG. 3. The peaks of the captured signals are designated with the letter c, the peaks of the fusion beats are designated with the letter f, and the intrinsic response is designated with the letter i. The peaks of the cardiac signals are clustered to form templates comprising one or more detection windows 430, 460, 470. Inclusion or exclusion of peaks from a detection window, or combinations of the detection windows 430, 460, 470 can be used to discriminate between the different cardiac responses.

FIG. 5 illustrates a first capture detection window 550, a second capture detection window 540 and an intrinsic detection window 560. In this example, midpoints 515, 525, 535 of the detection windows 550, 540, 560 are illustrated. The boundaries of the detection windows 550, 540, 560 may be calculated, for example, based on coordinates of characteristic features of the clustered cardiac signals.

In one implementation, an average of the characteristic feature coordinates may be defined as a point, such as a center, or other location, within a detection window. In this example, the boundaries of a detection window may be established according to a predetermined shape, for example, a circle, square, rectangle, rhombus, or other quadrilateral. Additionally or alternatively, a detection window may be created to enclose a predetermined area. After initialization of the detection windows 550, 540, 560, the detection windows may be used to detect a captured response, fusion/pseudofusion response and/or noncapture with intrinsic activation.

Figure 6:
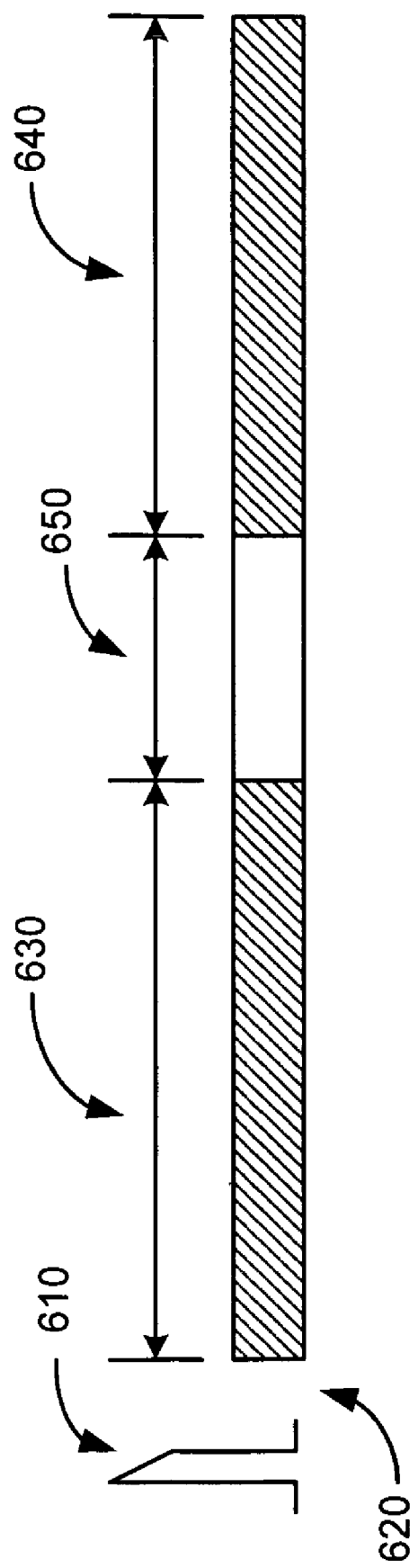
FIGS. 6 and 7 illustrate how detection windows formed by clustering can be used to detect various types of cardiac responses to pacing in accordance with embodiments of the invention.
Figure 7:
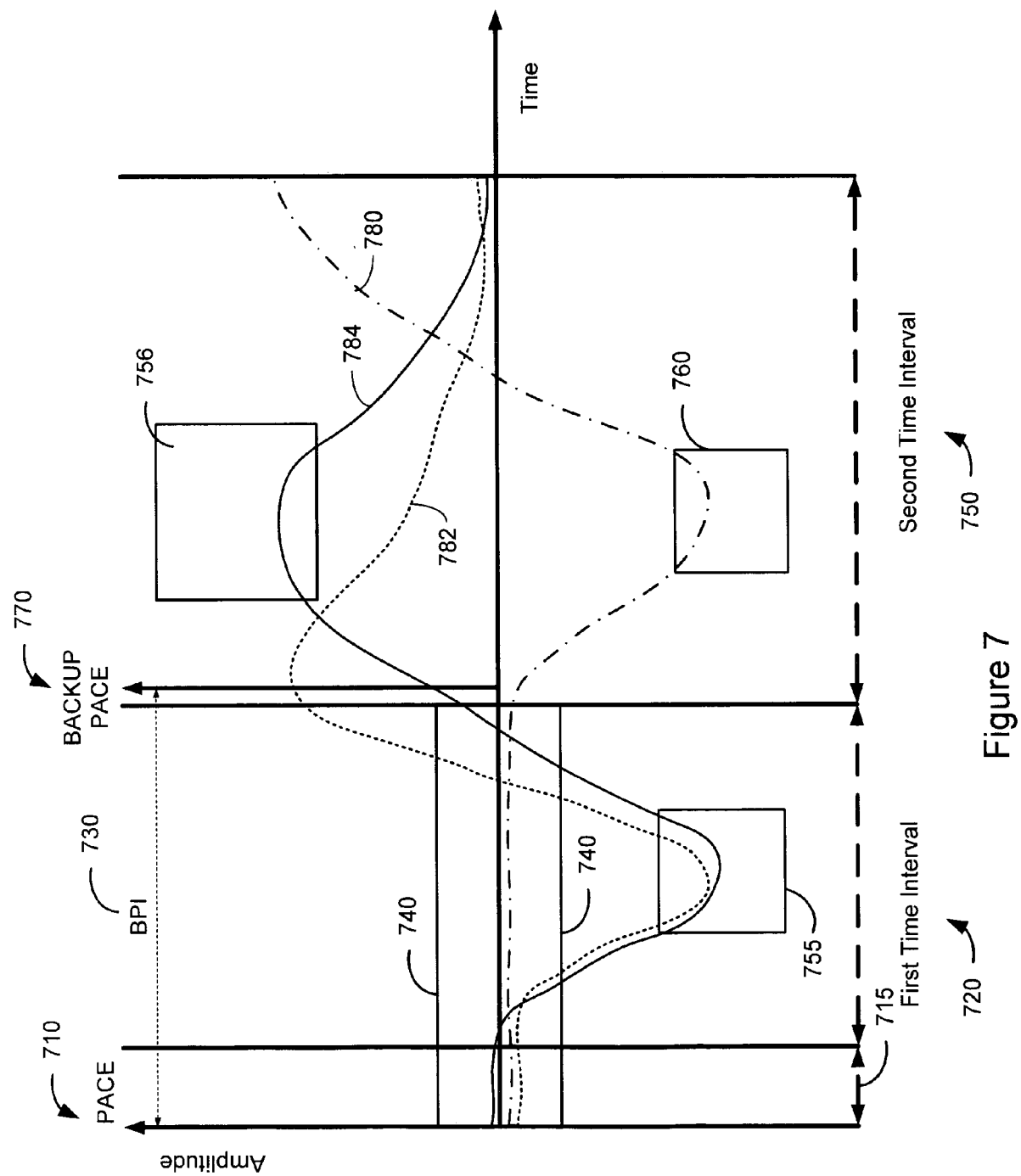

FIGS. 6 and 7 illustrate how detection windows formed by clustering can be used to detect various types of cardiac responses to pacing. A cardiac signal of a heart chamber sensed in one or multiple time intervals following a pacing pulse to the heart chamber may be used for determination of the cardiac pacing response in accordance with embodiments of the invention. As illustrated in FIG. 6, a pacing stimulation 610 is delivered to the heart, for example, to the right ventricle. The sensed cardiac signal is blanked for a period of time 620, typically about 0 milliseconds to about 40 milliseconds, following the delivery of the pacing pulse 610.

After the blanking period 620, the cardiac signal may be sensed in a first time interval 630. The duration of the first time interval 630 may be a programmable duration, for example, less than about 325 milliseconds. If the cardiac signal does not exceed a threshold in the first time interval 630, then the cardiac response may be classified as noncapture. If the cardiac signal exceeds a threshold value, then various characteristics or features of the cardiac signal may be extracted and compared to cardiac response templates for determining the type of cardiac pacing response. In some cases, sensing of the cardiac signal, associated feature extraction and template comparison may be extended to additional time intervals, such as the second time interval 640. The second time interval 640 may be programmable, and may have a duration less than about 325 milliseconds. The durations of the additional time intervals may be different or the same as the duration of the first time interval. Alternatively, the durations of the first and the second time intervals may be the same.

A delay period 650 may be established between the end of one time interval 230 and the beginning of another time interval 640. The duration of the delay may be in a range of about 0 milliseconds (no delay) to about 40 milliseconds, for example. The cardiac response to the pacing stimulation 610 may be classified based on the characteristics or features of the cardiac signal sensed in the first and/or the additional time intervals 630, 640, regarding their comparison to cardiac response templates.

FIG. 7 is a graph illustrating how templates formed using cardiac response detection windows, such as those illustrated in FIG. 5, may be used for capture detection. FIG. 7 illustrates includes superimposed graphs illustrating a captured response signal 784, a fusion response signal 782, and a non-captured intrinsic signal 780. Following delivery of a pace 710, the sensing channel is blanked, e.g., the sense electrodes are disconnected from sense amplifiers or the sense amplifiers are rendered inoperative, during a blanking period 715. Following the blanking period, the cardiac signal is sensed in one or more time intervals 720, 750. As illustrated in FIG. 6, sensing may occur in two time intervals following the pacing pulse. In some scenarios, the second 750 and subsequent time intervals (not shown) may be triggered by events occurring in one or more previous intervals.

In various implementations, sensing may be performed using the same electrode combination that was used to deliver the pacing stimulation. In other implementations, the pacing stimulation may be delivered using a first electrode configuration and sensing may use a second electrode configuration. Systems and methods for classifying a cardiac response to pacing using multiple time intervals and various sensing and pacing vectors are described in commonly owned U.S. patent applications Ser. No. 10/733,869, filed Dec. 11, 2003, entitled "Cardiac Response Classification Using Multiple Classification Windows"; Ser. No. 10/734,599 filed Dec. 12, 2003, entitled "Cardiac Response Classification Using Retriggerable Classification Windows"; and Ser. No. 10/735,519 filed Dec. 12, 2003, entitled "Cardiac Response Classification Using Multisite Sensing And Pacing"; which are hereby incorporated herein by reference.

During the first time interval 720, the system senses for a positive or negative cardiac signal magnitude exceeding a threshold level 740. If the cardiac signal magnitude does not exceed the threshold 740 during the first time interval 720, then the cardiac response is classified as noncapture and a backup pace 770 may be delivered. The backup pace 770 is typically a high energy pace that is delivered following a backup interval (BPI) 730. For example, the backup interval 730 may comprise an interval of about 100 ms timed from the delivery of the primary pace 710.

The system may utilize one or more cardiac response classification windows 755, 756, 760 for detecting various cardiac pacing responses. The template creation methods in accordance with embodiments of the invention may be used to form one or more of the classification windows 755, 756, 760. The cardiac response classification windows 755, 756, 760 are areas defined in terms of amplitude and time.

The system may classify a cardiac response as capture if a first peak value of the cardiac signal is detected in the first detection window 755 and a second peak value of the cardiac signal is detected in the second detection window 756. If a cardiac signal peak is detected in the intrinsic detection window 760, but not in the first or second capture detection windows 755, 756, the cardiac response may be classified as noncapture with early intrinsic activation. Otherwise, the cardiac response may be classified as a fusion/pseudofusion beat.

A template characterizing a particular type of cardiac pacing response may be adapted to accommodate gradual morphological changes in the cardiac pacing response. A cardiac signal waveform, e.g., a cardiac signal waveform representative of a captured response, may exhibit natural variations in its morphology over time. Unless the template is adjusted, the cardiac waveform morphology may gradually drift away from the originally established template.

In accordance with embodiments of the invention, one or more of the detection windows may be adjusted to accommodate changes in cardiac waveform morphology. A particular detection window may be adjusted according to a relationship, e.g., a spatial relationship, between the particular detection window and its associated waveform feature, for example a peak of the cardiac signal. Adjustment of the detection windows may involve, for example changing the size, shape, or location of the detection window.

A cardiac feature location, such as a peak, may be identified by a timing coordinate (usually represented as an x-axis coordinate) and an amplitude coordinate (y-axis coordinate). A detection window may be adjusted based on a relationship between a detected feature's amplitude coordinate and the associated detection window's amplitude range. A detection window may also be adjusted based on a relationship between an associated detected feature's timing coordinate and the detection window's timing range. In other examples, the detection window may be adjusted based on a variability of an associated detected feature's timing and/or amplitude coordinates.

According to embodiments of the invention, the adjustment of a detection window involves modifying the detection window in the direction of an associated cardiac feature location. In various examples, a detected cardiac feature may fall within a particular detection window, but be offset from the center of the detection window. The location, size, and/or shape of the detection window may be modified in the direction of re-centering or otherwise re-orienting the detection window with respect to an associated detected cardiac feature point falling within the detection window. The detection window may be adjusted, for example, using a function-based or rules-based technique.

According to one implementation, adjustment of the detection windows may be accomplished using a function that is based on present and past locations of an associated detected cardiac waveform feature, e.g., a peak. According to one example, the detection windows may be adjusted using an exponential average based on the present location of the waveform feature and the previous locations of the detection window. Adjustment of the detection window may be implemented based on Equation 1 below.

$$\text{Adjusted Location} = \alpha * \text{past location of the waveform feature} + (1-\alpha) * \text{present location of the waveform feature} \qquad [1]$$

By selecting the values of $\alpha$, more emphasis may be placed on the past location of the detection window, corresponding to $\alpha > 0.5$, or more emphasis may be placed on the present location of the waveform feature, corresponding to $\alpha < 0.5$. The value of $\alpha$ may vary for different features or characteristics. The location of the detection window may be determined by re-centering or otherwise re-orienting the detection window using the adjusted location.

In other implementations, a detection window may be adjusted using a rules-based technique. For example, the detection window may be adjusted in the direction of a detected associated feature point based on one or more re-centering rules.

A cardiac beat may be required to meet certain qualifications before it is used to adjust the detection windows. A cardiac beat qualified to adjust a detection window may be required to meet certain timing, rate, amplitude, regularity, or other criteria. The cardiac beat may be compared, for example, to a template representing a captured response. If the cardiac beat is consistent with the template, then the cardiac beat may be used to adjust one or more of the capture detection windows.

Figure 8B:
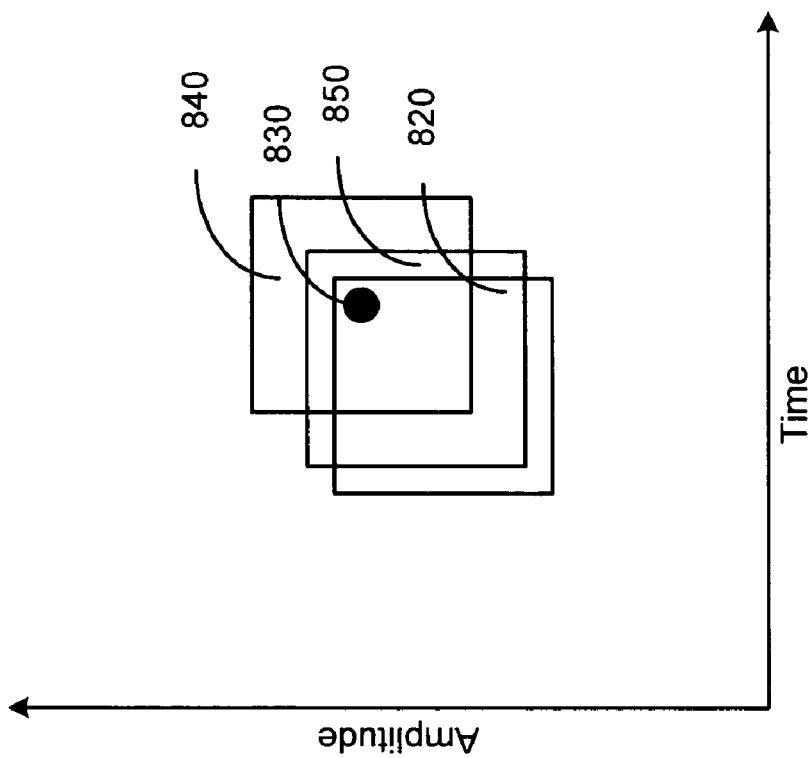
FIGS. 8A-8D illustrate adjustment of a detection window to accommodate for changes in cardiac signal morphology in accordance with embodiments of the invention.
Figure 8A:
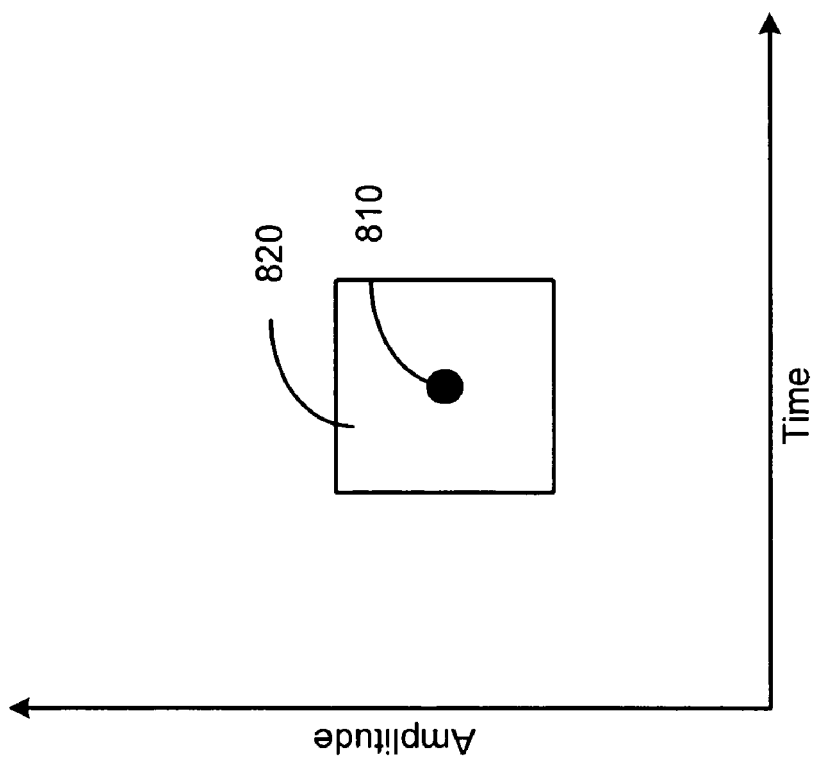

Adjustment of a detection window is illustrated in the diagrams of FIGS. 8A-B. FIG. 8A illustrates a detection window 820 having a center 810 based on locations of the previously detected cardiac waveform features associated with the detection window. FIG. 8B illustrates the situation after the next cardiac signal is sensed. The current cardiac waveform feature point 830 is detected. The location of the current feature point 830 has drifted above and to the right of the original center 810 illustrated in FIG. 8A. A current detection window 840 centered on the new cardiac waveform feature 830 would represent a significant change from the original detection window 820. In one example embodiment, adjustment of the detection window is performed so that modifications exhibit a relatively smooth transition. The adjusted detection window 850 may be determined, for example using Equation 1 or other method, to smoothly accommodate the waveform feature drift based on both the past detection window location 820 and the current detection window location 840. The adjustment of the detection window may be limited to predetermined upper and lower boundaries with respect to the amplitude and time coordinates.

Although Equation 1 mathematically describes adjusting the detection window location using an exponential average, other methods of adjusting the detection window locations are also possible. For example, in other embodiments, each of the one or more detection windows may be adjusted according to a moving window average, or another function representing the change in distance between the original detection window and the waveform feature. In a further embodiment, the detection windows may be adjusted according to a rules-based process. A rules-based adjustment process may involve adjusting the detection window location by an amount based on the locations of subsequently detected cardiac waveform features. For example, the detection window location may be moved an incremental amount to the right if a predetermined number, e.g., five, consecutive cardiac signals exhibit cardiac waveform features located within the detection window, but to the right of center of the original detection window. Adjustments in other directions, i.e., left, up, and down, may be made using similar criteria.

Figure 8D:
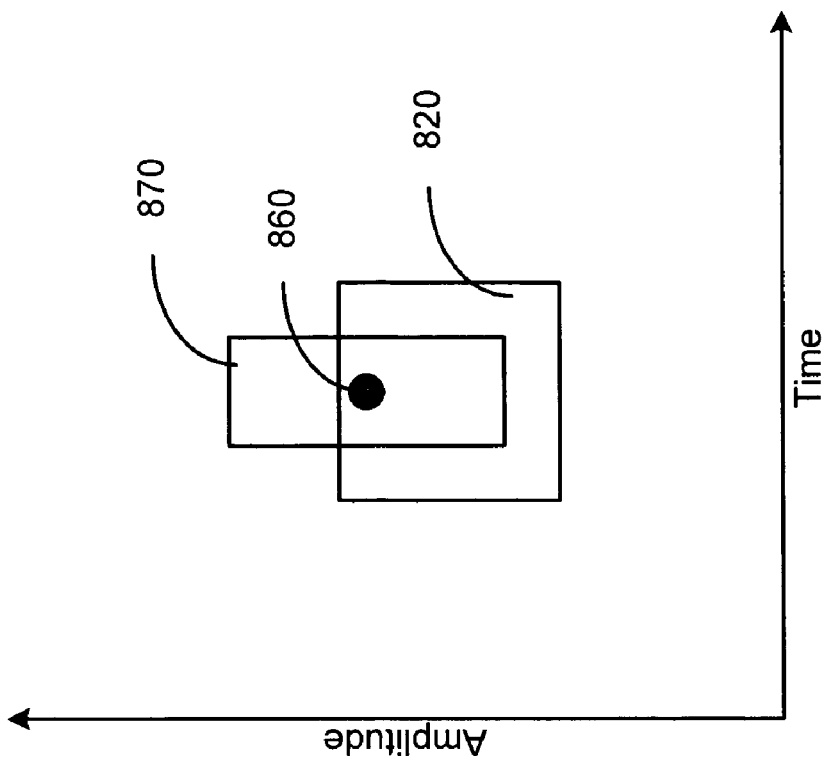
Figure 8C:
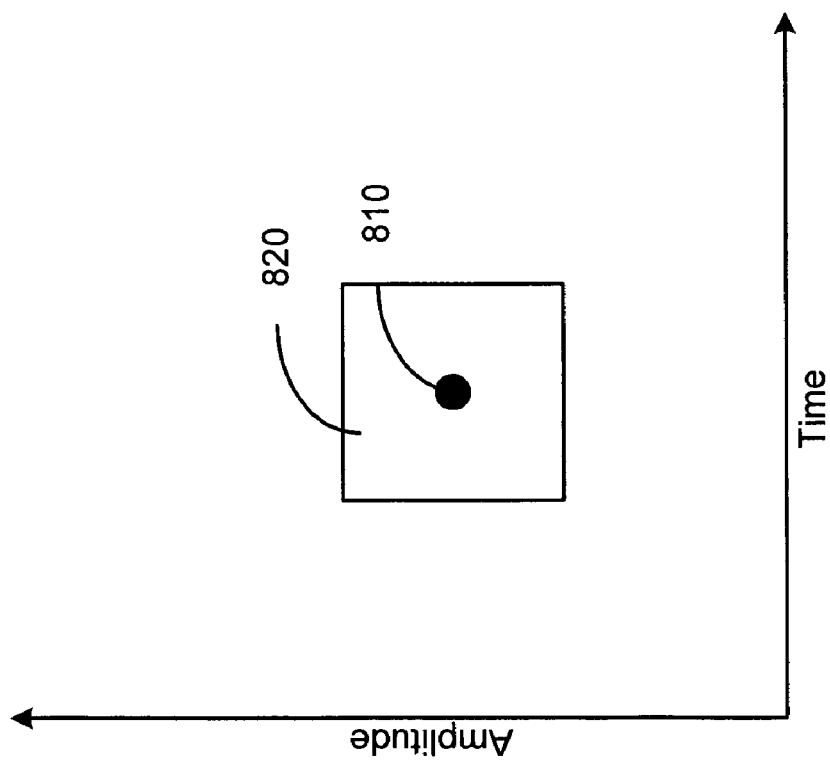

In yet other embodiments, adjustment of a detection window may include adjusting the shape and/or size of the detection window. FIGS. 8C-D are diagrams illustrating adjusting a detection window by modifying the shape of the detection window. FIG. 8C illustrates a detection window 820 having a center 810. FIG. 8D illustrates the situation after the next cardiac signal is sensed. The cardiac waveform feature 860 associated with the detection window 820 is detected. The location of the current feature point 860 has drifted above the original center 810 of the detection window 820. An adjusted detection window 870, having a different shape from the original detection window 820, is defined. The adjustment of the detection window may be limited to a predetermined limit. Methods and systems for updating detection windows, aspects of which may be used in connection with the present invention, are described in commonly owned U.S. Patent Application identified by Attorney Docket No. GUID.169PA, filed concurrently with this patent application, and incorporated herein by reference.

The embodiments of the present system illustrated herein are generally described as being implemented in an implantable cardiac defibrillator (ICD) that may operate in numerous pacing modes known in the art. Various types of single and multiple chamber implantable cardiac defibrillators are known in the art-and may be used in connection with cardiac devices and methods using cardiac waveform clustering for template generation in accordance with the present invention. The methods of the present invention may also be implemented a variety of implantable or patient-external cardiac rhythm management devices, including single and multi chamber pacemakers, defibrillators, cardioverters, bi-ventricular pacemakers, cardiac resynchronizers, and cardiac monitoring systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 9:
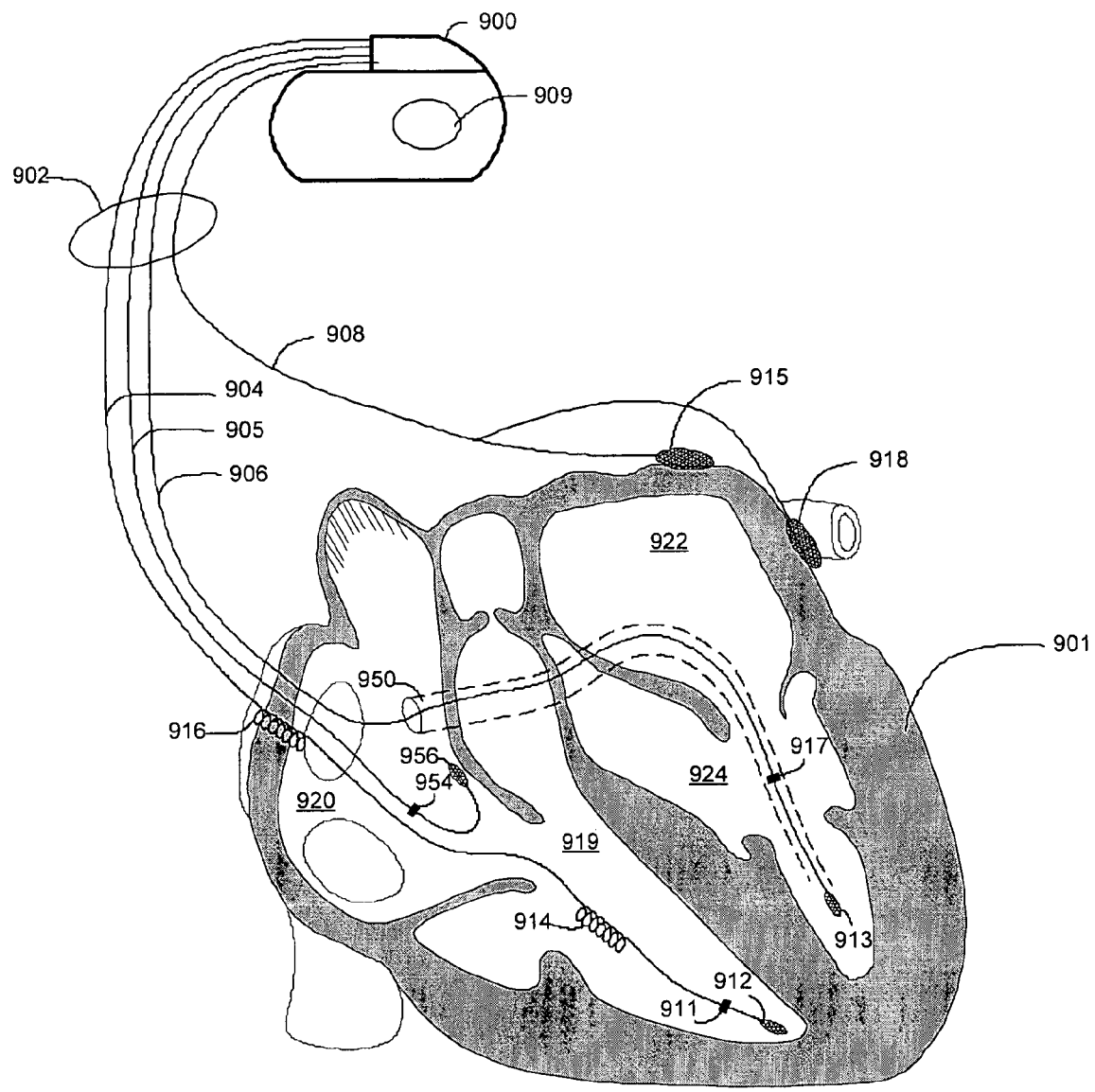
FIG. 9 illustrates a cardiac rhythm management device that may be used to implement template generation in accordance with embodiments of the present invention.

Referring now to FIG. 9 of the drawings, there is shown a cardiac rhythm management system that may be used to implement template generation methods of the present invention. The cardiac rhythm management system in FIG. 9 includes an cardiac rhythm management (CRM) device 900 electrically and physically coupled to a lead system 902. The housing and/or header of the CRM device 900 may incorporate one or more electrodes 909 used to provide electrical stimulation energy to the heart and to sense cardiac electrical activity. The CRM device 900 may utilize all or a portion of the CRM device housing as a can electrode 909. The CRM device 900 may also include indifferent electrodes (not shown) positioned, for example, on the header or the housing of the CRM device 900. If the CRM device 900 includes both a can electrode 909 and indifferent electrodes, the electrodes typically are electrically isolated from each other.

The lead system 902 is used to detect electric cardiac signals produced by the heart 901 and to provide electrical energy to the heart 901 under certain predetermined conditions to treat cardiac arrhythmias. The lead system 902 may include one or more electrodes used for pacing, sensing, and/or defibrillation. In the embodiment shown in FIG. 9, the lead system 902 includes an intracardiac right ventricular (RV) lead system 904, an intracardiac right atrial (RA) lead system 905, an intracardiac left ventricular (LV) lead system 906, and an extracardiac left atrial (LA) lead system 908. The lead system 902 of FIG. 9 illustrates one embodiment that may be used in connection with the template creation and cardiac response discrimination methodologies described herein. Other leads and/or electrodes may additionally or alternatively be used.

The lead system 902 may include intracardiac leads 904, 905, 906 implanted in a human body with portions of the intracardiac leads 904, 905, 906 inserted into a heart 901. The intracardiac leads 904, 905, 906 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 9, the lead system 902 may include one or more extracardiac leads 908 having electrodes, e.g., epicardial electrodes, positioned at locations outside the heart for sensing and pacing one or more heart chambers.

The right ventricular lead system 904 illustrated in FIG. 9 includes an SVC-coil 916, an RV-coil 914, an RV-ring electrode 911, and an RV-tip electrode 912. The right ventricular lead system 904 extends through the right atrium 920 and into the right ventricle 919. In particular, the RV-tip electrode 912, RV-ring electrode 911, and RV-coil electrode 914 are positioned at appropriate locations within the right ventricle 919 for sensing and delivering electrical stimulation pulses to the heart. The SVC-coil 916 is positioned at an appropriate location within the right atrium chamber 920 of the heart 901 or a major vein leading to the right atrial chamber 920 of the heart 901.

In one configuration, the RV-tip electrode 912 referenced to the can electrode 909 may be used to implement unipolar pacing and/or sensing in the right ventricle 919. Bipolar pacing and/or sensing in the right ventricle may be implemented using the RV-tip 912 and RV-ring 911 electrodes. In yet another configuration, the RV-ring 911 electrode may optionally be omitted, and bipolar pacing and/or sensing may be accomplished using the RV-tip electrode 912 and the RV-coil 914, for example. The right ventricular lead system 904 may be configured as an integrated bipolar pace/shock lead. The RV-coil 914 and the SVC-coil 916 are defibrillation electrodes.

The left ventricular lead 906 includes an LV distal electrode 913 and an LV proximal electrode 917 located at appropriate locations in or about the left ventricle 924 for pacing and/or sensing the left ventricle 924. The left ventricular lead 906 may be guided into the right atrium 920 of the heart via the superior vena cava. From the right atrium 920, the left ventricular lead 906 may be deployed into the coronary sinus ostium, the opening of the coronary sinus 950. The lead 906 may be guided through the coronary sinus 950 to a coronary vein of the left ventricle 924. This vein is used as an access pathway for leads to reach the surfaces of the left ventricle 924 which are not directly accessible from the right side of the heart. Lead placement for the left ventricular lead 906 may be achieved via subclavian vein access and a preformed guiding catheter for insertion of the LV electrodes 913, 917 adjacent to the left ventricle.

Unipolar pacing and/or sensing in the left ventricle may be implemented, for example, using the LV distal electrode referenced to the can electrode 909. The LV distal electrode 913 and the LV proximal electrode 917 may be used together as bipolar sense and/or pace electrodes for the left ventricle. The left ventricular lead 906 and the right ventricular lead 904, in conjunction with the CRM device 900, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 905 includes a RA-tip electrode 956 and an RA-ring electrode 954 positioned at appropriate locations in the right atrium 920 for sensing and pacing the right atrium 920. In one configuration, the RA-tip 956 referenced to the can electrode 909, for example, may be used to provide unipolar pacing and/or sensing in the right atrium 920. In another configuration, the RA-tip electrode 956 and the RA-ring electrode 954 may be used to provide bipolar pacing and/or sensing.

FIG. 9 illustrates one embodiment of a left atrial lead system 908. In this example, the left atrial lead 908 is implemented as an extracardiac lead with LA distal 918 and LA proximal 915 electrodes positioned at appropriate locations outside the heart 901 for sensing and pacing the left atrium 922. Unipolar pacing and/or sensing of the left atrium may be accomplished, for example, using the LA distal electrode 918 to the can 909 pacing vector. The LA proximal 915 and LA distal 918 electrodes may be used together to implement bipolar pacing and/or sensing of the left atrium 922.

Figure 10:
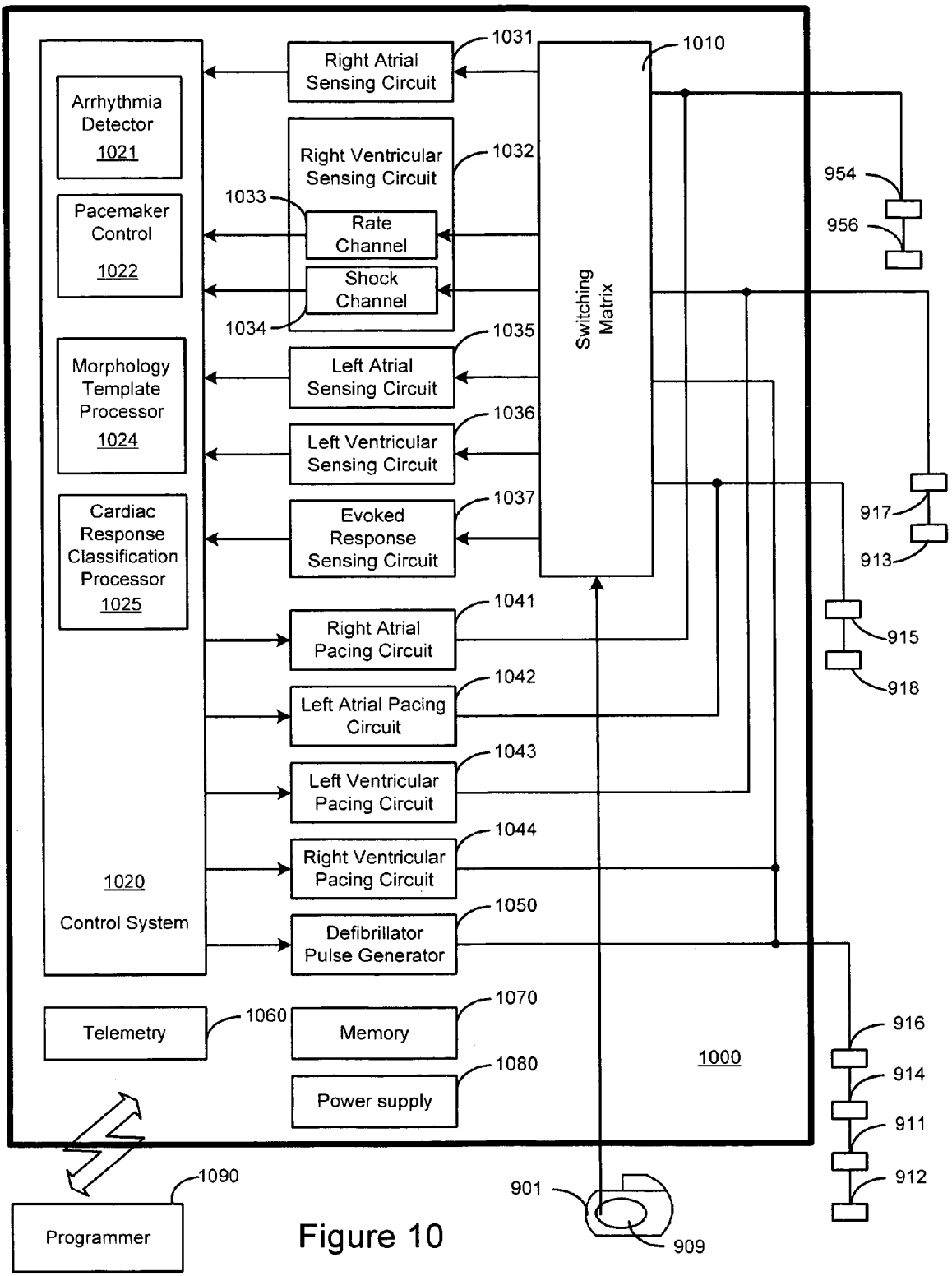
FIG. 10 illustrates a block diagram of a cardiac rhythm management (CRM) device suitable for implementing template formation and adaptation in accordance with embodiments of the present invention.

Referring now to FIG. 10, there is shown block diagram of a cardiac rhythm management (CRM) device 1000 suitable for implementing template formation and adaptation in accordance with embodiments of the present invention. FIG. 10 shows a CRM device divided into functional blocks. It is understood by those skilled in the art that there exist many possible configurations in which these functional blocks can be arranged. The example depicted in FIG. 10 is one possible functional arrangement. Other arrangements are also possible. For example, more, fewer or different functional blocks may be used to describe a cardiac defibrillator suitable for implementing the methodologies for forming templates according to the methodologies of the present invention. In addition, although the CRM device 1000 depicted in FIG. 10 contemplates the use of a programmable microprocessor-based logic circuit, other circuit implementations may be utilized.

The CRM device 1000 depicted in FIG. 10 includes circuitry for receiving cardiac signals from a heart and delivering electrical stimulation energy to the heart in the form of pacing pulses or defibrillation shocks. In one embodiment, the circuitry of the CRM device 1000 is encased and hermetically sealed in a housing 1001 suitable for implanting in a human body. Power to the CRM device 1000 is supplied by an electrochemical battery 1080. A connector block (not shown) is attached to the housing 1001 of the CRM device 1000 to allow for the physical and electrical attachment of the lead system conductors to the circuitry of the CRM device 1000.

The CRM device 1000 may be a programmable microprocessor-based system, including a control system 1020 and a memory 1070. The memory 1070 may store parameters for various pacing, defibrillation, and sensing modes, along with other parameters. The memory 1070 may be used, for example, for storing historical EGM and therapy data, and for retaining cardiac signals and/or cardiac signal features before and after grouping them with their associated clusters. The historical data storage may include, for example, data obtained from long-term patient monitoring used for trending or other diagnostic purposes. Historical data, as well as other information, may be transmitted to an external programmer unit 1090 as needed or desired.

The control system 1020 and memory 1070 may cooperate with other components of the CRM device 1000 to control the operations of the CRM device 1000. The control system depicted in FIG. 10 incorporates a template processor 1024 for forming cardiac response templates in accordance with various embodiments of the present invention. The control system 1020 may include additional functional components including a pacemaker control circuit 1022, a cardiac response classification processor 1025, and an arrhythmia detector 1021 along with other components for controlling the operations of the CRM device 1000.

Telemetry circuitry 1060 may be implemented to provide communications between the CRM device 1000 and an external programmer unit 1090. In one embodiment, the telemetry circuitry 1060 and the programmer unit 1090 communicate using a wire loop antenna and a radio frequency telemetric link, as is known in the art, to receive and transmit signals and data between the programmer unit 1090 and the telemetry circuitry 1060. In this manner, programming commands and other information may be transferred to the control system 1020 of the CRM device 1000 from the programmer unit 1090 during and after implant. In addition, stored cardiac data pertaining to capture threshold, capture detection and/or cardiac response classification, for example, along with other data, may be transferred to the programmer unit 1090 from the CRM device 1000.

The telemetry circuitry 1060 may provide for communication between the CRM device 1000 and an advanced patient management (APM) system. The advanced patient management system allows physicians to remotely and automatically monitor cardiac and/or other patient conditions. In one example, a CRM device may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In the embodiment of the CRM device 1000 illustrated in FIG. 10, electrodes RA-tip 956, RA-ring 954, RV-tip 912, RV-ring 911, RV-coil 914, SVC-coil 916, LV distal electrode 913, LV proximal electrode 917, LA distal electrode 918, LA proximal electrode 915, and can electrode 909 may be selectively coupled through a switch matrix 1010 to sensing circuits 1031-1037.

A right atrial sensing circuit 1031 serves to detect and amplify electrical signals from the right atrium of the heart. Bipolar sensing in the right atrium may be implemented, for example, by sensing voltages developed between the RA-tip 956 and the RA-ring 954. Unipolar sensing may be implemented, for example, by sensing voltages developed between the RA-tip 956 and the can electrode 909. Outputs from the right atrial sensing circuit are coupled to the control system 1020.

A right ventricular sensing circuit 1032 serves to detect and amplify electrical signals from the right ventricle of the heart. The right ventricular sensing circuit 1032 may include, for example, a right ventricular rate channel 1033 and a right ventricular shock channel 1034. Right ventricular cardiac signals sensed through use of the RV-tip 912 electrode are right ventricular near-field signals and are denoted RV rate channel signals. A bipolar RV rate channel signal may be sensed as a voltage developed between the RV-tip 912 and the RV-ring 911. Alternatively, bipolar sensing in the right ventricle may be implemented using the RV-tip electrode 912 and the RV-coil 914. Unipolar rate channel sensing in the right ventricle may be implemented, for example, by sensing voltages developed between the RV-tip 912 and the can electrode 909.

Right ventricular cardiac signals sensed through use of the RV-coil electrode 914 are far-field signals, also referred to as RV morphology or RV shock channel signals. More particularly, a right ventricular shock channel signal may be detected as a voltage developed between the RV-coil 914 and the SVC-coil 916. A right ventricular shock channel signal may also be detected as a voltage developed between the RV-coil 914 and the can electrode 909. In another configuration the can electrode 909 and the SVC-coil electrode 916 may be electrically shorted and a RV shock channel signal may be detected as the voltage developed between the RV-coil 914 and the can electrode 909/SVC-coil 916 combination.

Left atrial cardiac signals may be sensed through the use of one or more left atrial electrodes 915, 918, which may be configured as epicardial electrodes. A left atrial sensing circuit 1035 serves to detect and amplify electrical signals from the left atrium of the heart. Bipolar sensing and/or pacing in the left atrium may be implemented, for example, using the LA distal electrode 918 and the LA proximal electrode 915. Unipolar sensing and/or pacing of the left atrium may be accomplished, for example, using the LA distal electrode 918 to can vector 909 or the LA proximal electrode 915 to can vector 909.

A left ventricular sensing circuit 1036 serves to detect and amplify electrical signals from the left ventricle of the heart. Bipolar sensing in the left ventricle may be implemented, for example, by sensing voltages developed between the LV distal electrode 913 and the LV proximal electrode 917. Unipolar sensing may be implemented, for example, by sensing voltages developed between the LV distal electrode 913 or the LV proximal electrode 917 and the can electrode 909.

Optionally, an LV coil electrode (not shown) may be inserted into the patient's cardiac vasculature, e.g., the coronary sinus, adjacent the left heart. Signals detected using combinations of the LV electrodes, 913, 917, LV coil electrode (not shown), and/or can electrodes 909 may be sensed and amplified by the left ventricular sensing circuitry 1036. The output of the left ventricular sensing circuit 1036 is coupled to the control system 1020.

The outputs of the switching matrix 1010 may be operated to couple selected combinations of electrodes 911, 912, 913, 914, 915, 916, 917, 918, 956, 954 to an evoked response sensing circuit 1037. The evoked response sensing circuit 1037 serves to sense and amplify voltages developed using various combinations of electrodes for processes related to capture detection. For example, if the CRM device is implementing the process of forming a cardiac pacing response template, the evoked response sensing circuit may be coupled to the template processor 1024. The cardiac signals sensed by the evoked response sensing circuit 1037 may be used to form templates by clustering signals or signal features indicative of various cardiac pacing responses in accordance with embodiments of the invention.

During capture verification and/or capture threshold testing the evoked response sensing circuit 1037 may be coupled to the cardiac response classification processor 1025. Signals sensed by the evoked response sensing circuit 1037 via various electrode combinations may be analyzed by the cardiac response classification processor 1025 for detecting capture and/or other responses to cardiac pacing as described herein. Other sensing circuits may alternatively be used for template formation and/or detecting cardiac pacing responses.

In the embodiments described below, various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing.

The pacemaker control circuit 1022, in combination with pacing circuitry for the left atrium, right atrium, left ventricle, and right ventricle 1041, 1042, 1043, 1044, may be implemented to selectively generate and deliver pacing pulses to the heart using various electrode combinations. The pacing electrode combinations may be used to effect bipolar or unipolar pacing of the heart chambers as described above.

Bipolar or unipolar pacing pulses may be delivered to a heart chamber via the pacing vectors described above. The electrical signal following the delivery of the pacing pulses may be sensed through various sensing vectors coupled through the switch matrix 1010 to the evoked response sensing circuit 1037 or other sensing circuits and used to classify the cardiac response to pacing.

In one example, the cardiac signal following the pacing pulse may be sensed using the same vector as was used for delivery of the pacing pulse. In this scenario, the pacing artifact may be canceled or otherwise removed or minimized from the sensed cardiac signal. Following cancellation of the pacing artifact, one or more time intervals and cardiac response classification windows may be defined following the pacing pulse and used to classify the cardiac response to pacing. The cardiac response may be classified as one of a captured response, a non-captured response, a non-captured response with intrinsic activation, and a fusion/pseudofusion beat, for example.

In another example, the vector used to sense the cardiac signal following the pacing pulse may be different from the vector that was used to deliver the pacing pulse. The sensing vector may be selected to minimize the pacing artifact. Cancellation of the pacing artifact may not be necessary if the pacing artifact is sufficiently minimized using this technique.

In various embodiments, the pacing vector may be a near-field vector and the sensing vector may be a far-field vector. In an example of right ventricular pacing and cardiac response sensing, the pacing vector may be the rate channel vector and the sensing vector may be the shock channel vector.

Subcutaneous electrodes may provide additional sensing vectors useable for template formation and cardiac response classification. In one implementation, cardiac rhythm management system may involve a hybrid system including an intracardiac device configured to pace the heart and an extracardiac device, e.g., a subcutaneous defibrillator, configured to perform functions other than pacing. The extracardiac device may be employed to detect and classify cardiac response to pacing based on signals sensed using subcutaneous electrode arrays. The extracardiac and intracardiac devices may operate cooperatively with communication between the devices occurring over a wireless link, for example. Examples of subcutaneous electrode systems and devices are described in commonly owned U.S. patent applications Ser. No. 10/462,001, filed Jun. 13, 2003 and Ser. No. 10/465,520, filed Jun. 19, 2003, which are hereby incorporated herein by reference in their respective entireties.

The methods and systems described in the embodiments provided herein use cardiac signal features to generate, update, and/or use cardiac response templates. Although the examples provided are described in terms of generating, updating, and using morphology templates for cardiac pacing response determination, the principles of the invention may be additionally or alternatively applied to the generation and/or use of other types of cardiac morphology templates.

For example, cardiac beats produced during an arrhythmic episode may have characteristic features that can be discriminated from the features of normal beats. In one scenario, the suspected arrhythmic beats may be compared to a morphology template characterizing a normal beat morphology. Arrhythmia is confirmed if the sensed beat morphology is sufficiently different from the normal beat morphology. In another scenario, a sensed arrhythmic beat may be compared to one or more templates associated with different types of monomorphic arrhythmias. The type of monomorphic arrhythmia experienced by the patient may be determined based on the similarity of the cardiac beats of the arrhythmia to one of the morphology templates.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system for characterizing types of cardiac pacing responses, comprising:
 a pulse generator configured to deliver pacing pulses to a heart;
 a sensor system configured to sense cardiac signals following delivery of the pacing pulses;
 a template processor configured to extract features of the cardiac signals and to cluster the features into a plurality of clusters, the processor further configured to select one or more predominant clusters from the plurality of clusters and to form a captured response template using the predominant clusters, and to select one or more less predominant clusters and to form an additional template characterizing a pacing response other than capture using the one or more less predominant clusters; and
 a memory configured to store the captured response template and the additional template.

2. The system of claim 1, wherein the template processor is configured to cluster the features using one or both of K-means clustering and a self-organizing map algorithm.

3. The system of claim 1, wherein the template processor is configured to form an initial template using features of an initial cardiac signal and to modify the initial template using features of additional cardiac signals if the features of the additional cardiac signals are sufficiently similar to the initial template.

4. The system of claim 1, wherein the additional template formed using the less predominant clusters is associated with fusion.

5. The system of claim 1, wherein the additional template formed using the less predominant clusters is associated with intrinsic activation.

6. The system of claim 1, wherein the additional template formed using the less predominant clusters is associated with noise.

7. The system of claim 1, wherein the captured response template comprises a detection window associated with a cluster of negative peaks of the cardiac signals and a detection window associated with a cluster of positive peaks of the cardiac signals.

8. The system of claim 1, wherein the template processor is configured cluster each feature of a cardiac signal with similar features independently of other features of the cardiac signal.

9. The system of claim 1, wherein N cardiac signals are sensed following N pacing pulses and the processor is configured to form the captured response template using the predominant clusters if features of a predetermined number of the N cardiac signals are associated with the dominant clusters.

10. The system of claim 1, wherein the template processor is further configured to store information related to pacing energy with each of the templates.

11. The system of claim 10, wherein the information includes pacing voltage.

12. The system of claim 10, wherein the information includes pulse width.

13. The system of claim 1, wherein the template processor is further configured to store information related to pacing rate with each of the templates.

14. The system of claim 1, wherein the processor is further configured to store information related to a pacing interval with each of the templates.

15. The system of claim 14, wherein the pacing interval comprises an atrioventricular delay.

16. The system of claim 14, wherein the pacing interval comprises a ventricular pacing interval.

17. The system of claim 1, wherein:
 the captured response template comprises a first capture detection window and a second capture detection window;
 the first capture detection window is associated with a first predominant cluster of first peaks of the cardiac signals;
 the second capture detection window is associated with a second predominant cluster of second peaks having opposite polarity from the first peaks;
 the additional template comprises an intrinsic template comprising an intrinsic detection window; and
 the intrinsic detection window is associated with a less predominant cluster of peaks of the cardiac signals, wherein each of the detection windows has positive and negative amplitude boundaries and positive and negative time boundaries.

18. The system of claim 17, further comprising a classification processor configured to classify a subsequent cardiac signal as a captured response if peaks of the subsequent cardiac signal fall within both of the captured response detection windows and to classify the subsequent cardiac signal as an intrinsic activation if a peak of the subsequent cardiac signal falls within the intrinsic detection window, and to classify the subsequent cardiac signal as fusion if peaks of the subsequent cardiac signal do not fall within both of the capture detection windows and do not fall within the intrinsic detection window.

19. The system of claim 18, wherein the subsequent cardiac signal is sensed in a first time interval and a second time interval following the pacing pulse and one of the captured response detection windows occurs within the first time interval and another of the captured response detection windows occurs within the second time interval.

20. The system of claim 19, wherein the second time interval is triggerable based on an event occurring in the first time interval.

21. The system of claim 1, wherein:
the pulse generator is configured to deliver the pacing pulses using a first electrode configuration; and
the sensing system is configured to sense the cardiac signals using a second electrode configuration that is different from the first electrode configuration.

* * * * *